(12) United States Patent
Ciccone et al.

(10) Patent No.: US 10,758,301 B2
(45) Date of Patent: Sep. 1, 2020

(54) HIGHLY MANEUVERABLE DISPOSABLE RESECTOSCOPE

(71) Applicant: Boston Surgical Arts LLC, Chestnut Hill, MA (US)

(72) Inventors: Joseph Michael Ciccone, Chestnut Hill, MA (US); Howard Zaretsky, Rochester, NY (US)

(73) Assignee: Boston Surgical and Endoscopic, LLC, Chestnut Hill, MA (US)

( * ) Notice: Subject to any disclaimer, the term of this patent is extended or adjusted under 35 U.S.C. 154(b) by 463 days.

(21) Appl. No.: 15/806,444

(22) Filed: Nov. 8, 2017

(65) Prior Publication Data
US 2018/0125567 A1 May 10, 2018

Related U.S. Application Data

(60) Provisional application No. 62/419,467, filed on Nov. 9, 2016.

(51) Int. Cl.
*A61B 18/12* (2006.01)
*A61B 18/14* (2006.01)
(Continued)

(52) U.S. Cl.
CPC ........ *A61B 18/149* (2013.01); *A61B 1/00066* (2013.01); *A61B 1/00105* (2013.01);
(Continued)

(58) Field of Classification Search
CPC ............ A61B 17/00234; A61B 18/149; A61B 2017/0023; A61B 2017/00274;
(Continued)

(56) References Cited

U.S. PATENT DOCUMENTS

| 5,133,713 A | 7/1992 | Huang et al. |
| 5,441,042 A | 8/1995 | Putman |
| 5,456,684 A * | 10/1995 | Schmidt ................. A61B 17/29 604/35 |
| 5,643,294 A * | 7/1997 | Tovey ..................... A61B 17/29 606/148 |
| 5,902,300 A | 5/1999 | Hahnen et al. |

(Continued)

FOREIGN PATENT DOCUMENTS

| JP | 2008093019 | 4/2008 |
| WO | WO2016/040478 A1 | 3/2016 |

OTHER PUBLICATIONS

International Search Report issued in PCT/US2017/060503 dated Feb. 27, 2018.
(Continued)

*Primary Examiner* — Daniel W Fowler
(74) *Attorney, Agent, or Firm* — Zaretsky Group PC; Howard Zaretsky

(57) ABSTRACT

A novel and useful highly maneuverable and disposable resectoscope having a working element such that surgeons are able to more comfortably perform transurethral resections. The resectoscope permits the surgeon to resect anywhere on the bladder or prostate wall while keep their hand in an ergonomic position. This results in more comfortable surgery that causes less fatigue for the surgeons as well a quicker, safer, and more effective operation. The disposable resectoscope includes a completely disposable design, an analog or digital optics system, a handle that is independently rotatable from the remainder of the resectoscope, a rotation mechanism that can independently rotate an electrocautery electrode and optical lens independent of the handle rotation, and a repositioning of surgical cords and cables for a more comfortable hand placement.

25 Claims, 24 Drawing Sheets

(51) Int. Cl.
*A61B 1/307* (2006.01)
*A61B 1/00* (2006.01)
*A61B 1/015* (2006.01)
*A61B 17/00* (2006.01)
*A61B 17/29* (2006.01)
*A61B 18/00* (2006.01)

(52) U.S. Cl.
CPC .......... *A61B 1/00133* (2013.01); *A61B 1/015* (2013.01); *A61B 1/307* (2013.01); *A61B 17/00234* (2013.01); *A61B 2017/0023* (2013.01); *A61B 2017/00274* (2013.01); *A61B 2017/00358* (2013.01); *A61B 2017/00424* (2013.01); *A61B 2017/291* (2013.01); *A61B 2018/00184* (2013.01); *A61B 2018/1475* (2013.01); *A61B 2217/007* (2013.01)

(58) Field of Classification Search
CPC .......... A61B 2017/00358; A61B 2017/00424; A61B 2017/291
See application file for complete search history.

(56) References Cited

U.S. PATENT DOCUMENTS

| | | |
|---|---|---|
| 6,142,931 A | 11/2000 | Kaji |
| 6,805,664 B2 | 10/2004 | Doyle et al. |
| 6,830,545 B2 | 12/2004 | Bendall |
| 7,169,147 B2 | 1/2007 | Nosel |
| 7,192,396 B2 | 3/2007 | Boulais |
| 2004/0044343 A1* | 3/2004 | Brommersma ...... A61B 18/149 606/46 |
| 2011/0066148 A1* | 3/2011 | Hamou ............ A61B 18/1485 606/41 |
| 2011/0295066 A1 | 12/2011 | Fan |
| 2015/0351777 A1 | 12/2015 | Lizardi et al. |
| 2016/0128838 A1 | 5/2016 | Assell et al. |

OTHER PUBLICATIONS

Written Opinion issued in PCT/US2017/060503 dated Feb. 27, 2018.
International Search Report issued in PCT/US2015/049180 dated Dec. 4, 2015.

* cited by examiner

HIGHLY MANEUVERABLE DISPOSABLE RESECTOSCOPE

REFERENCE TO PRIORITY APPLICATION

This application claims the benefit of U.S. Provisional Application No. 62/419,467, filed Nov. 9, 2016, entitled "Disposable Resectoscope," incorporated herein by reference in its entirety.

FIELD OF THE DISCLOSURE

The subject matter disclosed herein relates to the field of medical instruments and more particularly relates to a highly maneuverable and disposable resectoscope.

BACKGROUND OF THE INVENTION

Transurethral resection (TUR) is common practice in urologic surgery and is employed in the treatment of conditions affecting the lower urinary channel, including the urethra, prostate, and bladder. More than 150,000 TUR procedures are performed in the U.S. each year to cut out bladder tumors or reduce enlarged prostates. The primary tool for conducting a TUR is a transurethral resectoscope, a surgical instrument that employs an electrode to cut and cauterize tissue. It is a type of endoscope, an instrument that combines a camera and instrumentation that allows surgeons to view and perform surgery through a small incision or orifice.

The resectoscope is a surgical tool designed to be inserted into the urethra to treat conditions related to the prostate or bladder in a minimally invasive fashion. Traditionally, a resectoscope consists of an assembly of components that when put together, make up a full resectoscope. These parts include a working element, a long lens, electrocautery electrode (loop), inner sheath, and an outer sheath. Once fully assembled the user, i.e. the surgeon, inserts the resectoscope into a patient's body to perform the surgery.

The resectoscope's cutting element has a fixed orientation with respect to the handle, meaning that the surgeon has to rotate the handle of the tool in order to reach each cutting area. On many operations, the doctor needs to operate on all walls of the prostate or bladder, which requires a 360-degree rotation of the resectoscope handle. Due to the limited rotation of the surgeon's hand, they are forced to switch to their non-dominant hand or hold the handle upside down. Since the resectoscope is not designed for this, the surgeon's grip on the tool in these positions is less comfortable and results in lower precision. Outside of the ergonomic 90-degrees of rotation achievable by most doctors, they have to operate in an awkward, inefficient, and imprecise position. The result is a less effective, more dangerous, and longer surgery.

The conventional resectoscope is designed as a reusable device, which is normally sterilized after each use, and then repurposed for another patient. This re-sterilization and repurposing can be costly and time consuming, and holds the risk of cross-contaminating resistant organisms from one patient to another. This is especially pertinent in an age where resistant organisms are currently on the rise.

Additionally, the way a conventional resectoscope is designed restricts a surgeon during certain positions. Often surgeons are required to resect in a 360-degree field. However, due to the natural movement of a human wrist, a surgeon is often limited when these positions require him or her to rotate their hand fully counterclockwise.

In response to this uncomfortable hand movement, surgeons often compensate by holding the handle in the opposite hand, or upside down, which is not the intended use of the resectoscope. This unintended hand positioning on a resectoscope can make a surgeon's hand movements unsteady and imprecise, which can put a patient at risk. Additionally, the surgeon's hand is restricted by the presence of irrigation, power for a light source, and camera cables or cords which often get in the way when a surgeon attempts to rotate the resectoscope in 360-degree space.

Considering the above, there is thus a need for an improved resectoscope whose features address the issues of cost effectiveness, patient safety, and surgeon comfort. In addition, there is a need for a resectoscope that is designed to be disposable.

SUMMARY OF THE INVENTION

The present invention is a highly maneuverable and disposable resectoscope having a working element such that surgeons are able to more comfortably perform transurethral resections. The device is appropriate for both Transurethral Resection of Bladder Tumors (TURBT) and Transurethral Resection of the Prostate (TURP). It permits the surgeon to resect anywhere on the bladder or prostate wall while keep their hand in an ergonomic position. This results in more comfortable surgery that causes less fatigue for the surgeons as well a quicker, safer, and more effective operation.

The following disclosure relates to a disposable surgical device (i.e. a resectoscope) and its related components that includes (1) a completely disposable design, (2) an analog or digital optics system, (3) a handle that is independently rotatable from the remainder of the resectoscope, (4) a rotation mechanism (i.e. knob) that can independently rotate an electrocautery electrode (i.e. loop) and optical lens independent of the handle rotation, (5) a repositioning of surgical cords and cables for a more comfortable hand placement, and (6) a virtually wireless, tubeless design.

The design of the resectoscope of the present invention promotes numerous benefits for surgeons, including (1) superior ergonomics, (2) improved procedural efficiency, (3) limiting potential complications, (4) minimizing equipment costs through independent control of the electrode while other components are kept stationary so that the surgeon can perform more precise resections/vaporizations, and (5) enhancing and accelerating the learning curve of the surgical resident or post-graduate surgeon.

In addition, since the resectoscope is disposable, there is no need for laborious cleaning or reprocessing steps, ongoing maintenance, or repairs. This is especially beneficial in today's healthcare environment where bacterial cross-contamination of reusable medical devices is a major concern. Another benefit of the resectoscope is that is can.

Furthermore, the resectoscope reduces the overall costs of the resection/vaporization procedure by improving procedural efficiencies, minimizing complications and readmissions, lowering equipment purchasing costs, and virtually eliminating reprocessing, maintenance, and repair costs.

The disposable resectoscope described infra is advantageous in many ways. Making the design disposable decreases the cost associated with re-sterilizing, repurposing and restocking conventional reusable equipment which makes the disposable resectoscope more cost effective overall. Additionally, the disposable resectoscope eliminates the risk of cross-contaminating resistant organisms from one patient to another. Making the optics completely digital removes the need for having a bulky camera attached to the lens of the resectoscope, which emancipates space for a surgeon's hand to move more freely, and in turn removes a cable that would ordinarily be in the same space as the surgeon's hand.

A rotatable handle alleviates the uncomfortable grip a surgeon may have when over-pronating their wrist in a counter clockwise motion, and negate the need for switching hands, or holding the handle upside-down, thus increasing steadiness and maintaining a surgeon's hand in a grip that was originally intended. The knob which is attached to the loop and optical lens allows both components to rotate independently from the rest of the resectoscope offering the same advantages in surgeon comfort pertaining to hand positioning. Moreover, the repositioning of cables and wires in and out of the resectoscope allows more freedom for the surgeon to operate unencumbered, and allows for the outer sheath of the resectoscope to be clipped into a stationary place within the operating field to prevent unnecessary translational torque from the scope to the patient's body.

It is noted that the resectoscope disclosed herein has application not only to the field of urology but also to gynecology (e.g., hysteroscopy resection or fibroids, etc.) and a variety of other fields including laparoscopic surgery, robotic surgery, anesthesia (e.g., endotracheal intubation, bronchoscopy, etc.), and other surgical fields, including veterinary. In addition, the principles of the present invention also have application outside of the medical field.

This, additional, and/or other aspects and/or advantages of the embodiments of the present invention are set forth in the detailed description which follows; possibly inferable from the detailed description; and/or learnable by practice of the embodiments of the present invention.

There is thus provided in accordance with the invention, a surgical device, comprising a conduit having a longitudinal axis and being configured to extend into a body cavity, a handle rotatably coupled to the conduit, a surgical tool aligned parallel to the longitudinal axis of the conduit and capable of both rotating within and selectively extending from the conduit, and a rotation mechanism coupled to the surgical tool, the rotation mechanism configured to enable a user to control the rotation of the surgical tool independent of a position of the handle.

There is also provided in accordance with the invention, a surgical device comprising a base ring having an inner portion, outer portion and side portion, an outer sheath having a longitudinal axis and configured to extend into a body cavity, the outer sheath affixed to the side portion of the base ring and having inlet and outlet irrigation ports, an inner sheath having a longitudinal axis and placed within the outer sheath, the inner sheath rotatably coupled to the inner portion of the base ring, a surgical tool located within the inner sheath, a handle rotatably coupled to the outer portion of the base ring, a collar affixed to the surgical tool, a rotation knob coupled to the collar whereby rotation of the knob causes rotation of the inner sheath and surgical tool independent of rotation of the handle, and a trigger coupled to the collar whereby lateral motion of the trigger causes lateral motion of the surgical tool while the inner sheath remains stationary.

There is further provided in accordance with the invention, a method for examination or treatment within a body cavity of a patient utilizing a surgical device, wherein the surgical device comprises a conduit having a longitudinal axis and being configured to extend into the body cavity, a handle rotatably coupled to the conduit, a surgical tool aligned parallel to the longitudinal axis of the conduit and capable of both rotating within and selectively extending from the conduit, a rotation mechanism coupled to the surgical tool, the rotation mechanism configured to enable a user to control the rotation of the surgical tool independent of a position of the handle, the method comprising inserting the surgical device into the body cavity of the patient such that the surgical device extends therein, gripping the handle in a relatively comfortable position regardless of the position of the surgical tool, and rotating the surgical tool to a desired position independent of a position of the handle.

There is also provided in accordance with the invention, a surgical device, comprising a conduit having a longitudinal axis and being configured to extend into a body cavity, a handle rotatably coupled to the conduit, a surgical tool aligned parallel to the longitudinal axis of the conduit and capable of both rotating within and selectively extending laterally from the conduit, a trigger coupled to the surgical tool and adapted to provide a user lateral control of the surgical tool intendent of rotation thereof, a rotation mechanism coupled to the surgical tool, the rotation mechanism configured to enable a user to control the rotation of the surgical tool independent of a position of the handle and lateral extension of the surgical tool via said trigger.

BRIEF DESCRIPTION OF THE DRAWINGS

The present invention is explained in further detail in the following exemplary embodiments and with reference to the figures, where identical or similar elements may be partly indicated by the same or similar reference numerals, and the features of various exemplary embodiments being combinable. The invention is herein described, by way of example only, with reference to the accompanying drawings, wherein.

DETAILED DESCRIPTION

Figure 1:
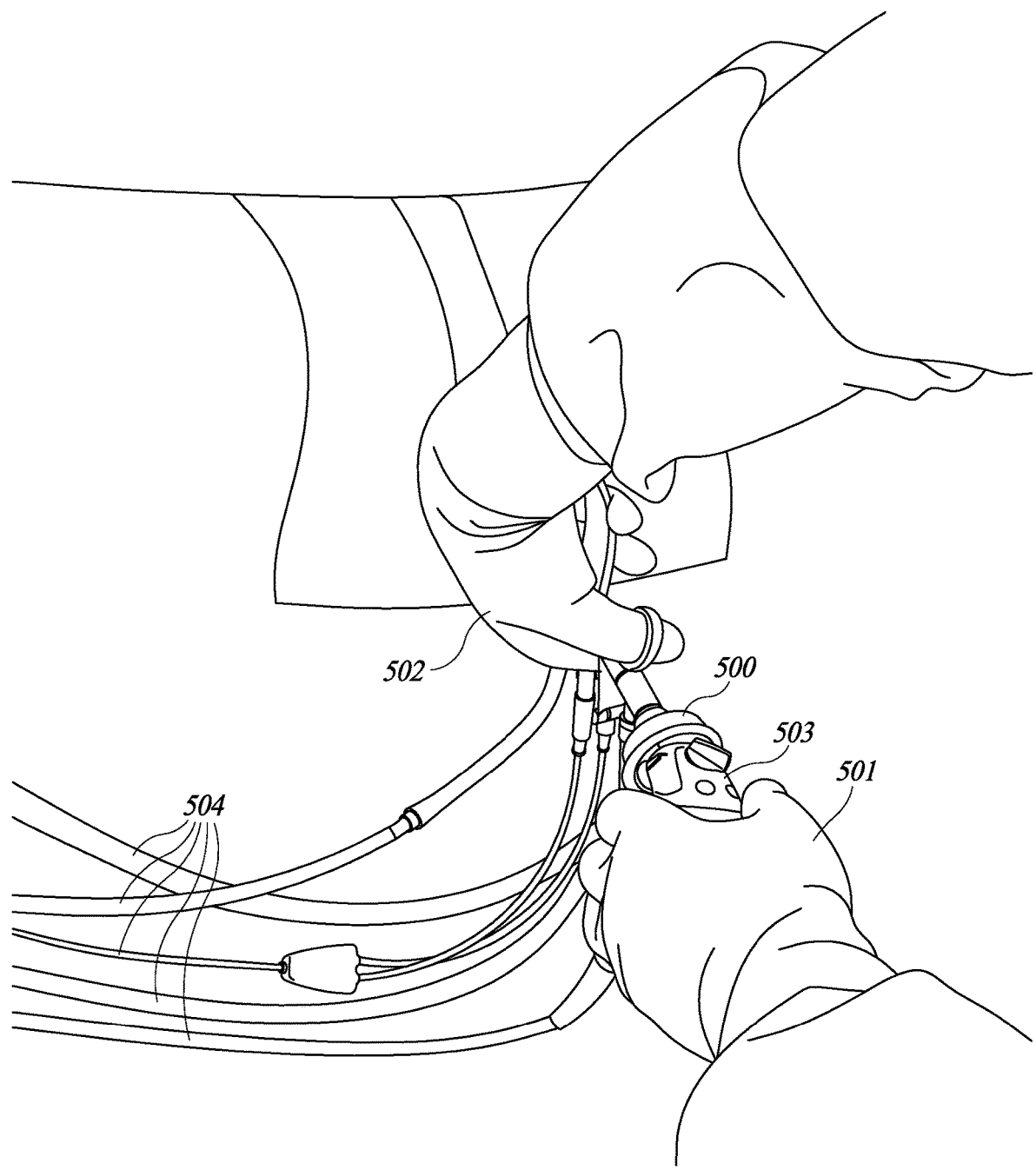
FIG. 1 is a diagram illustrating an example unnatural orientation for a prior art resectoscope in use by a surgeon.

In the following detailed description, numerous specific details are set forth in order to provide a thorough understanding of the invention. It will be understood by those skilled in the art, however, that the present invention may be practiced without these specific details. In other instances, well-known methods, procedures, and components have not been described in detail so as not to obscure the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary, for the understanding and appreciation of the underlying concepts of the present invention and in order not to obfuscate or distract from the teachings of the present invention.

Any reference in the specification to a method should be applied mutatis mutandis to a system capable of executing the method. Any reference in the specification to a system should be applied mutatis mutandis to a method that may be executed by the system.

Throughout the specification and claims, the following terms take the meanings explicitly associated herein, unless the context clearly dictates otherwise. The phrases "in one embodiment," "in an example embodiment," and "in some embodiments" as used herein do not necessarily refer to the same embodiment(s), though it may. Furthermore, the phrases "in another embodiment," "in an alternative embodiment," and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

The present invention is a disposable resectoscope that allows a surgeon's hand to remain in an ergonomically neutral position while treating lesions anywhere within the lower urinary tract. Additionally, a cord containment system allows all cordage to remain stationary, freeing the surgeon from the frustration of cord entanglement. The cord containment system internalizes within a body all of the resectoscope's mechanical, optical, and electrical systems. By obviating the need for a camera head at the tail end of the resectoscope, a rotation knob allows the surgeon's non-dominant hand to rotate the electrode loop and telescope to the desired position while the resectoscope itself remains stationary. The invention also allows the optical cable, water inflow and outflow tubes, and cautery wire to remain fixed, thereby freeing the surgeon of all cordage, and creating 'virtually wireless' resection experience. Utilizing disposable materials permits higher performance to be achieved without the cost and infectious risk of prior art reusable resectoscopes.

A diagram illustrating an example unnatural orientation for a prior art resectoscope in use by a surgeon is shown in FIG. 1. The surgeon's right hand 502 is shown controlling the resectoscope 500. The surgeon's left hand 501 is holding an imaging device 503. A plethora of cables and irrigation hoses 504 extend from the resectoscope. The position of the surgeon's left hand is awkward and causes the over pronation of the surgeon's wrist in a counter-clockwise motion. In such positions, the surgeon must hold the handle of the resectoscope upside down or other non-natural position thus decreasing steadiness and forcing the surgeon's hand to hold the resectoscope in an unnatural grip.

Figure 2A:
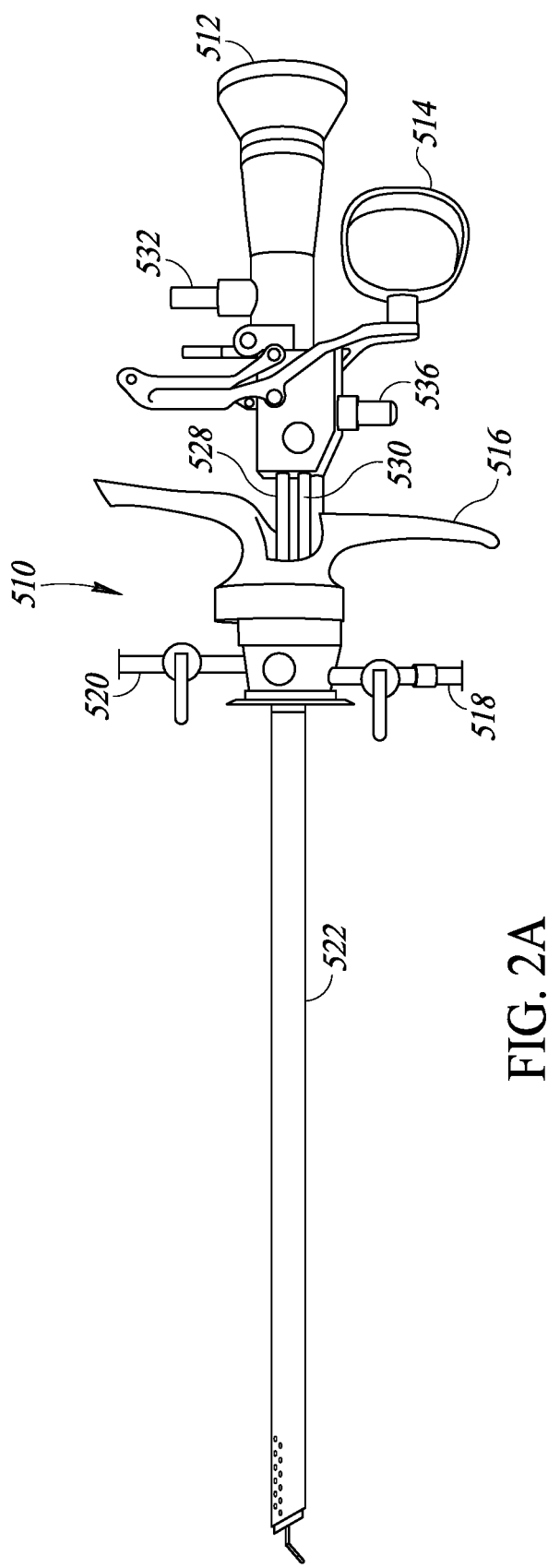
FIG. 2A is a diagram illustrating a side view of an example prior art resectoscope.

A diagram illustrating a side view of an example prior art resectoscope is shown in FIG. 2A. The resectoscope, generally referenced 510, comprises an outer sheath 522, scope (i.e. eyepiece or viewport) 512, optical fiber light source connector 532, thumb rest 514, optical tube 528, electrode tube 530, handle 516, irrigation inlet 520, irrigation outlet 518, and electrode electrical connector 536. The outer sheath and inner sheath comprise conduits able to be inserted into a body cavity of a patient. Within these conduits pass several components including the optical tube, electrical supply cable for the electrode loop and in some embodiments cables for LED lighting, imaging sensor devices, etc.

Figure 2B:
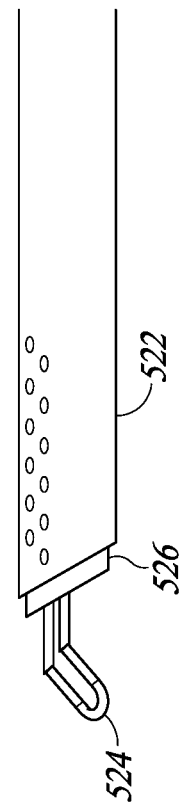
FIG. 2B is a diagram illustrating the electrode loop end of the prior art resectoscope is more detail.

A diagram illustrating the electrode loop end of the prior art resectoscope is more detail is shown in FIG. 2B. The end portion of the resectoscope comprises outer sheath 522, inner sheath 526 and electrode loop 524.

Figure 2C:
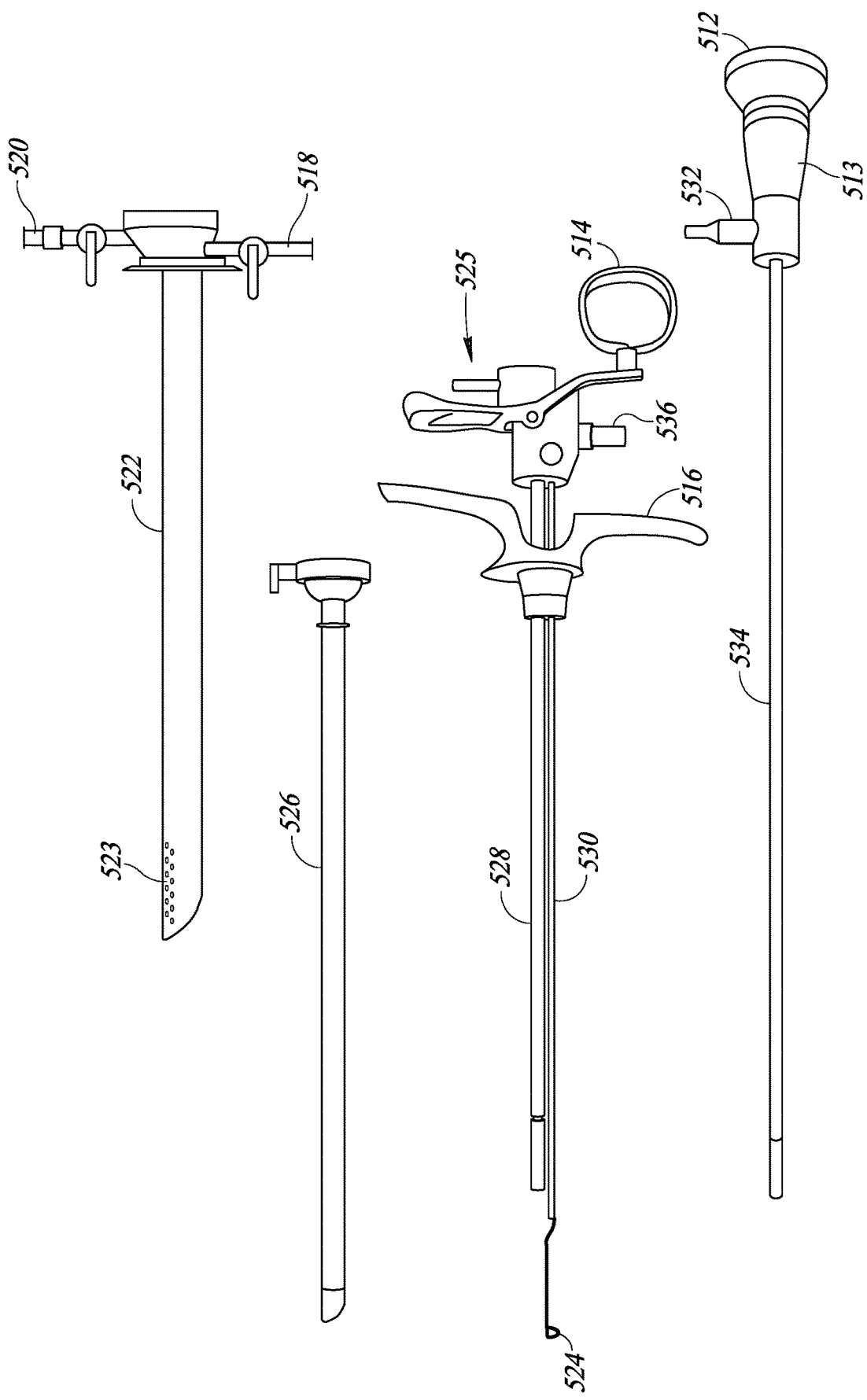
FIG. 2C is a diagram illustrating several component parts making up an example prior art resectoscope.

A diagram illustrating several component parts making up an example prior art resectoscope is shown in FIG. 2C. The outer sheath 522 comprises a plurality of perforations 523 for water flow and inlet and outlet irrigation connectors. The inner sheath 526 is adapted to slide into the outer sheath. The optical tube 528, electrode wire tube 530, and electrode loop 524 are adapted to slide into the inner sheath 526. The tube portion 534 of the scope 512 is adapted to slide into optical tube 528. Illuminating light is provided by an external source and coupled to the scope via optical fiber connected to the scope via connector 532.

The assembled and disassembled resectoscope consists of a scope 512, working element 525 with bonded inner sheath, outer sheath, and electrode. The resectoscope comprises a scope 512, a working element 525 including a handle 516, a thumb rest 514, a surgical tool (i.e. cutting element, electrode, etc.) 524, an inner sheath 526, an outer sheath 522, inflow and outflow irrigation ports 518, 520. The scope 512 is inserted through the working element 525 and a scope tube 528. The scope 512 includes a light port 523 for connection to an optical light source. Optics 513 provides the surgeon with a view of the working area at the end of the scope. The cutting element 524 is inserted through the working element and the electrode support tube 530. The inner sheath 526 attaches to the resectoscope 510 over the scope tube 534, and the outer sheath 522 attaches to the resectoscope over the inner sheath 526. The working element, the sheath assembly, the cutting element, and the telescope are rotationally fixed relative to each other.

The resectoscope 510 includes a trigger mechanism to produce a controlled linear movement of the cutting element along the longitudinal axis of the device. As a user engages the trigger mechanism, the cutting element 524, e.g., an electrode tip and/or sharp surface, extends from the outer sheath 522 to the targeted tissue surface. The cutting element is heated and is brought into contact with the targeted tissue. As the user releases the trigger mechanism, the cutting element 524 retracts into the outer sheath 522 and the targeted tissue is severed.

In some embodiments, the surgical tool, e.g., cutting element, 524 can have an arcuate shape, e.g., a looped shape. Tissue removal is achieved by reciprocation of the cutting element 524, and thus the cutting element is reoriented to each new tissue section.

Figure 3:
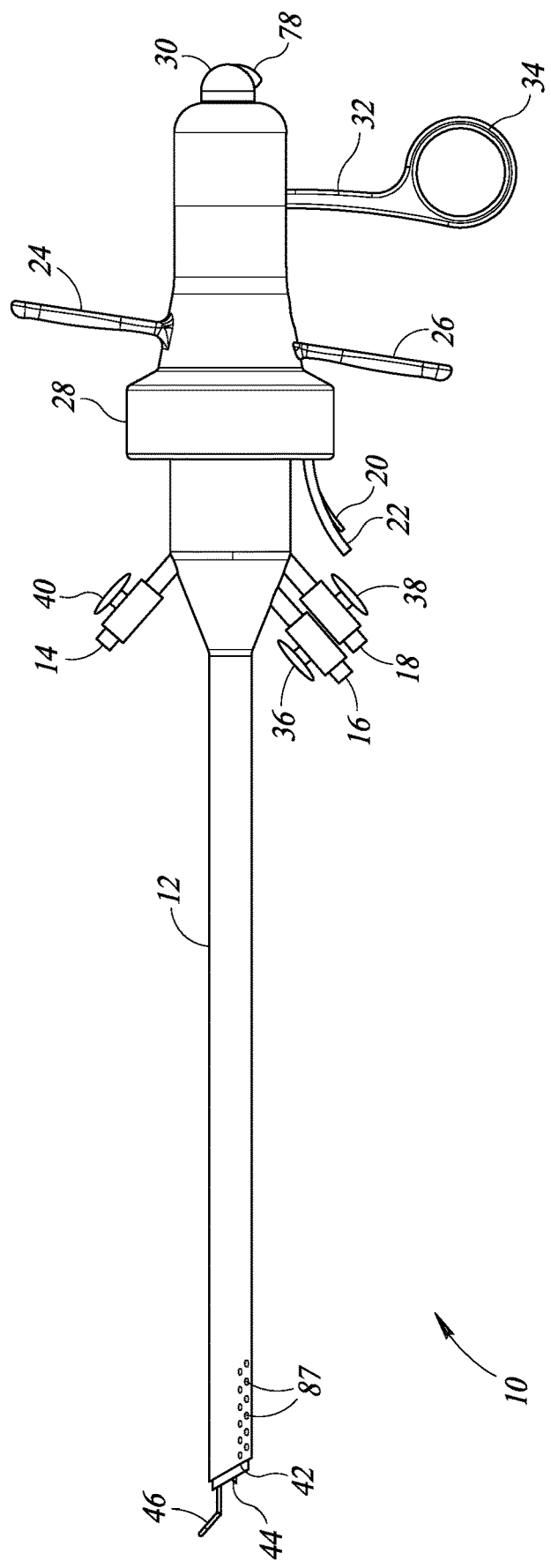
FIG. 3 is a diagram illustrating a side view of an example resectoscope of the present invention.
Figure 4:
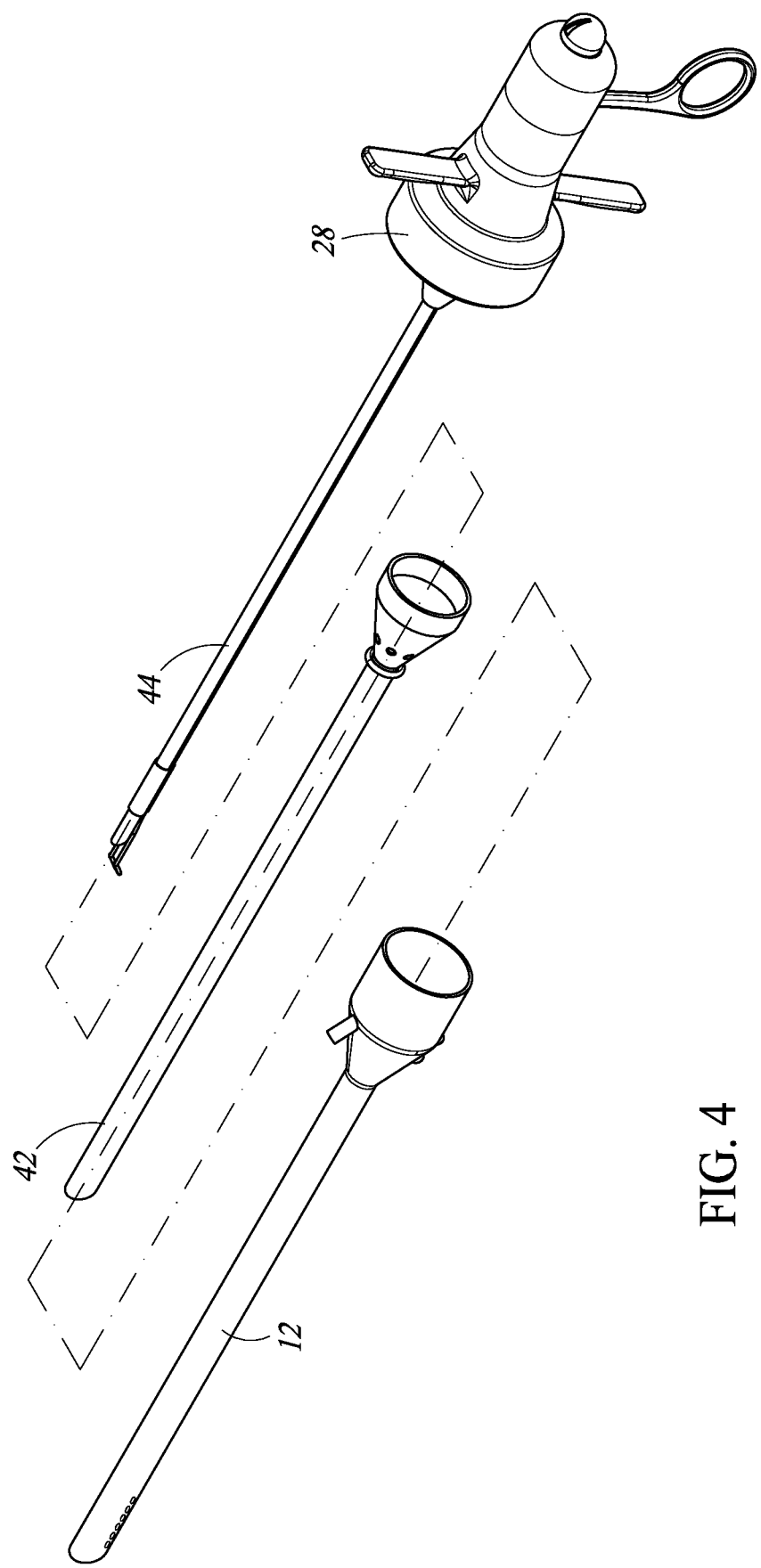
FIG. 4 is a diagram illustrating several components making up an example resectoscope of the present invention.

A diagram illustrating a side view of an example resectoscope of the present invention is shown in FIG. 3. A diagram illustrating several components making up an example resectoscope of the present invention is shown in FIG. 4. A diagram illustrating a cutaway view of an example resectoscope of the present invention is shown in FIG. 5.

Figure 5:
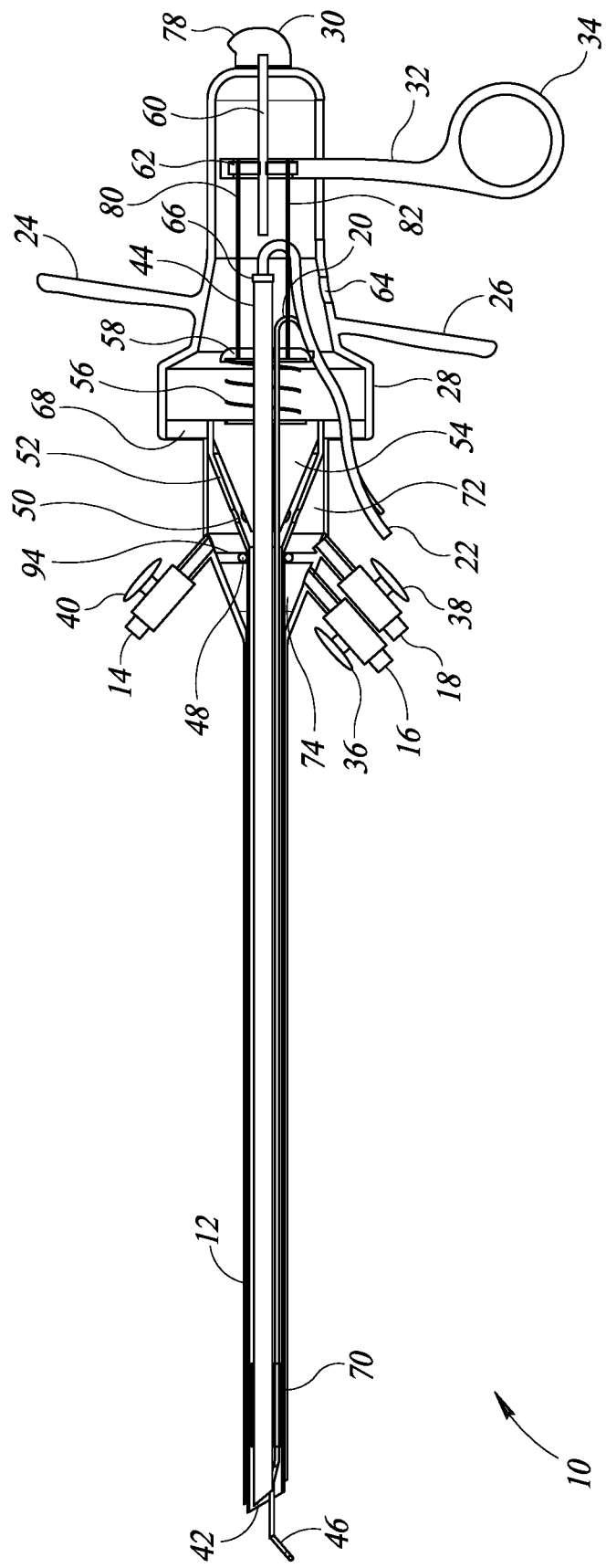
FIG. 5 is a diagram illustrating a cutaway view of an example resectoscope of the present invention.

With reference to FIGS. 3, 4, and 5, the resectoscope, generally referenced 10, comprises an outer sheath 12, inner sheath 42, optical tube 44 having a lens incorporated in its tip, inlet irrigation tubes 14, 18 with corresponding valves 40, 38, optical cable 22, electrical cable 20 for supplying power to the surgical tool (i.e. electrode or loop) 46, handle assembly 28 including finger rests 24, 26, loop control 32 including thumb hole 34, and rotation knob 30 including rotation position indicator 78. The optical tube 44 and electrode are adapted to slide into the inner sheath 42 which is adapted to slide into the outer sheath 12.

The optical tube 44 as well as the electrical cable pass through collar 58, spring 56 and cone 54. They extend past cone 54 through the inside of the inner sheath 42. The inner sheath, in turn, lies inside the outer sheath 12 and can move both laterally and rotationally inside the outer sheath. In normal operation, the loop 46, optical tube 44 and inner sheath 42 are configured to rotate together in unison. The loop, however, is configured to move laterally along the axis of the inner sheath independent of the position of the optical tube and inner sheath.

When in use, water or other solution used for irrigating the bladder enters the inflow cavity 72 of the outer sheath 12 via one or both of inlet tubes 14, 18 and valve 40, 38, respectively. Inflow cavity 72 is separated from outflow cavity 74 by partition wall 94 and O-ring 96. Irrigation fluid flows from the inflow cavity 72 through a plurality of holes 50 in the inner sheath 42 into the inside of the inner sheath. The fluid travels the length of the inner sheath to exit from the left end of the inner sheath into the bladder or other working area or organ of the body.

Return fluid enters the outer sheath via a plurality of holes 98 in the left end of the outer sheath 12. The return fluid travels the length of the outer sheath in the space between the outside wall of the inner sheath and the inside wall of the outer sheath to reach the inner cavity 74 where it exits through exit tube 16 and valve 36. Note that the fluid that enters cavity 96 is prevented from leaking via tight sealing between the cone 54 and the end portion of the inner sheath. In one embodiment, the end portion of the inner sheath is affixed to the cone and together they rotate as a single entity.

The inner sheath, however, is fitted to the inner portion of base ring 68. The outer portion of the base ring is fitted to the handle 28. The handle can freely rotate around the outside of the base ring. In addition, the inner sheath can freely rotate around the inside of the base ring. The interface between the inner sheath, handle, and base ring may comprise any suitable lubricant, grease, silicon, coating, bearings, dry lubricant, etc. The right end of the outer sheath is detachably or permanently affixed to the front facing wall of the base ring while the inner sheath is free to rotate within the outer sheath. The optical cable 22 and loop power cable 20 pass through the wall of the base ring 68. The above features allow the outer sheath with all irrigation tubes, optical and electrical cables to remain stationary while the inner sheath 42, optical tube 44 and loop 46 all rotate together as a single entity. This permits the surgeon to freely select a desired orientation of the handle 28 independently of the position of the inner sheath, optical tube and loop.

Rotation of the combination of inner sheath, optical tube and loop is achieved by rotating a knob 30 at the right end of the handle 28. A pointer 78 on the knob 30 indicates the orientation of the combination. As part of the rotation mechanism, rotating knob 30 causes central shaft 60, fastened to knob 30, to rotate. The central shaft 60 passes through inner disk 62 which is configured to rotate freely within the trigger 32 which incorporates thumb rest 34. In one embodiment, the central shaft is shaped such that rotational energy imparted by the knob is transferred to the inner disk 62. This can be accomplished by configuring the central shaft to include, for example, a square shape, a key, or other suitable mechanical features to transfer rotation from the knob to the inner disk. The inner disk 62 sits within the trigger 32 and is able to freely rotate therein.

Rotational energy from the inner disk 62 in the trigger 32 is transferred to the collar 58 via one or more pins 80, 82 (two are shown in this example embodiment). Thus, turning the knob 30 causes shaft 60 to turn, which causes the inner ring to turn, which causes the collar to rotate via the pins which are affixed to the inner disk and the collar. The collar is affixed to the optical tube as well as the loop power cable. In addition, both the optical tube as well as the loop power cable are affixed to the cone 54. Thus, when the collar rotates, the optical tube, loop power cable, cone and inner sheath all rotate as well. The optical cable 22 is connected to the optical tube 44 by an optical rotary joint or swiveable optical coupler or connecter 66. Thus, regardless of the position of the optical tube 44, the optical cable remains stationary. Note, however, that the loop power cable can freely move laterally through the cone 54 but is affixed to the collar 58.

In one embodiment, the resectoscope of the present invention also provides lateral movement of the loop along the axis of the inner sheath. Lateral movement of the trigger by a surgeon's thumb is transferred to the loop 46 via the pins 80, 82 (e.g., thin metal rods) coupled to the collar 58. Back and forth movement of the trigger causes the inner disk to move laterally which in turn causes the collar to move laterally as well since they are connected to one another via the one or more pins 80, 82. Note that lateral movement of the collar only causes the power cable and loop to move laterally. The collar is able to slideably move along the optical tube and thus does not move laterally with the collar lateral movement. Note that resistance to lateral movement of the loop is provided by spring 56 which is seated between a depression in the right end of the cone 54 and a depression in the left side of the collar 58. Thus, movement of the trigger 32 to the right causes the spring 56 to compress while the loop is extended out to the right of the inner sheath. Removal of force on the trigger allows the spring to decompress and cause the loop to retract within the inner sheath.

Note that the trigger 32 moves laterally within the handle 28 through an opening or slit 76 on the bottom of the handle. In addition, an access hole 64 is provided in the wall of the handle for a user to access a release pin 92 in the side of the collar 58. Pressing the pin 92 releases the loop assembly from the collar allowing it to be removed and replaced with a new or different one.

FIGS. 6-15 illustrate different views of the resectoscope with (1) the trigger in various positions of loop extension and retraction; and (2) the knob in various rotation positions.

Figure 6:
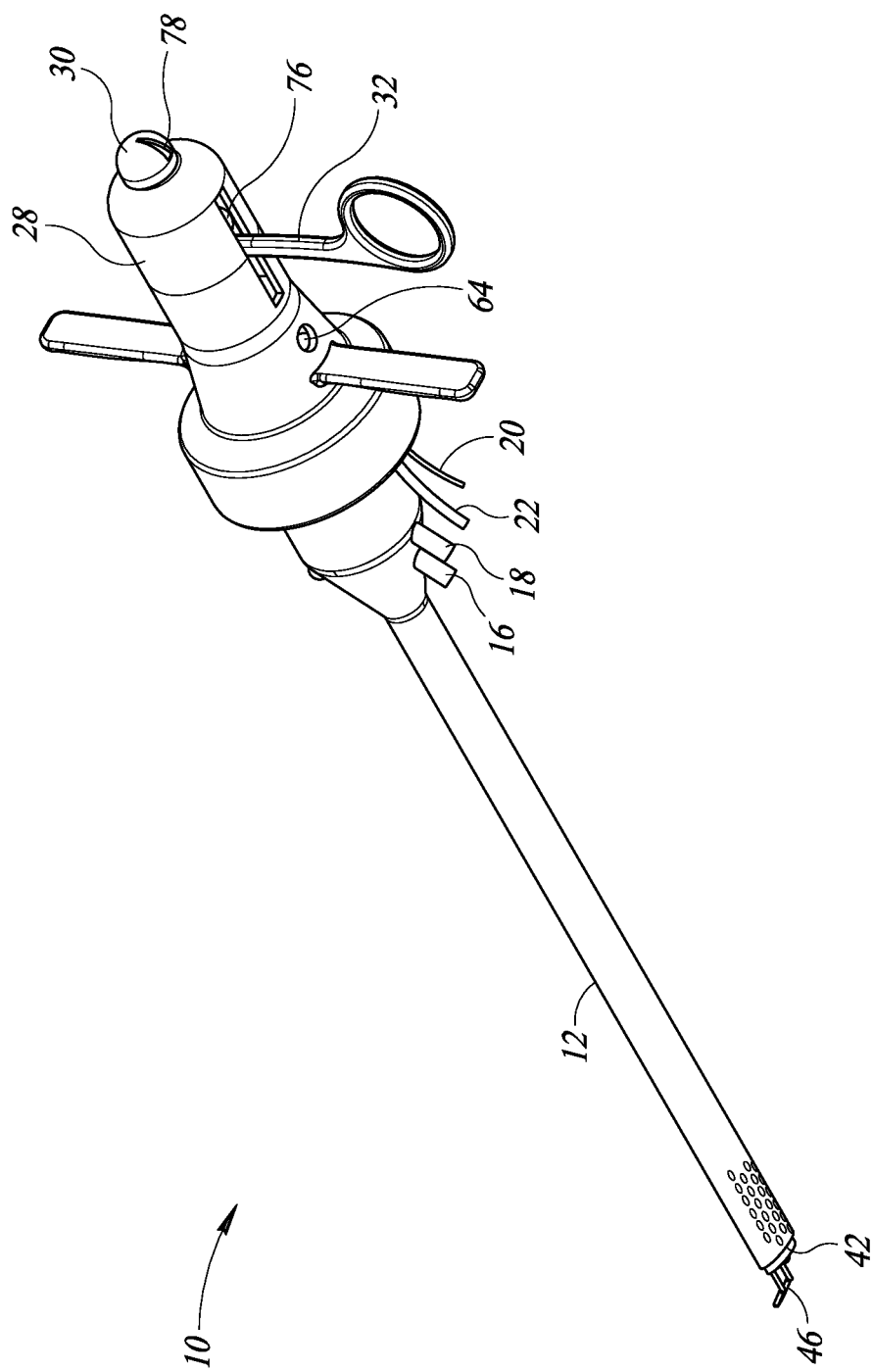
FIG. 6 is a diagram illustrating a perspective view of an example resectoscope of the present invention with the surgical tool retracted and rotated to a first position.

A diagram illustrating a perspective view of an example resectoscope of the present invention with the surgical tool retracted and rotated to a first position is shown in FIG. 6. With reference to FIG. 6, the loop 46 and knob 30 of the resectoscope 10 are rotated 180 degrees from the position shown in FIG. 5. In addition, the loop 46 is shown in retracted position.

Figure 7:
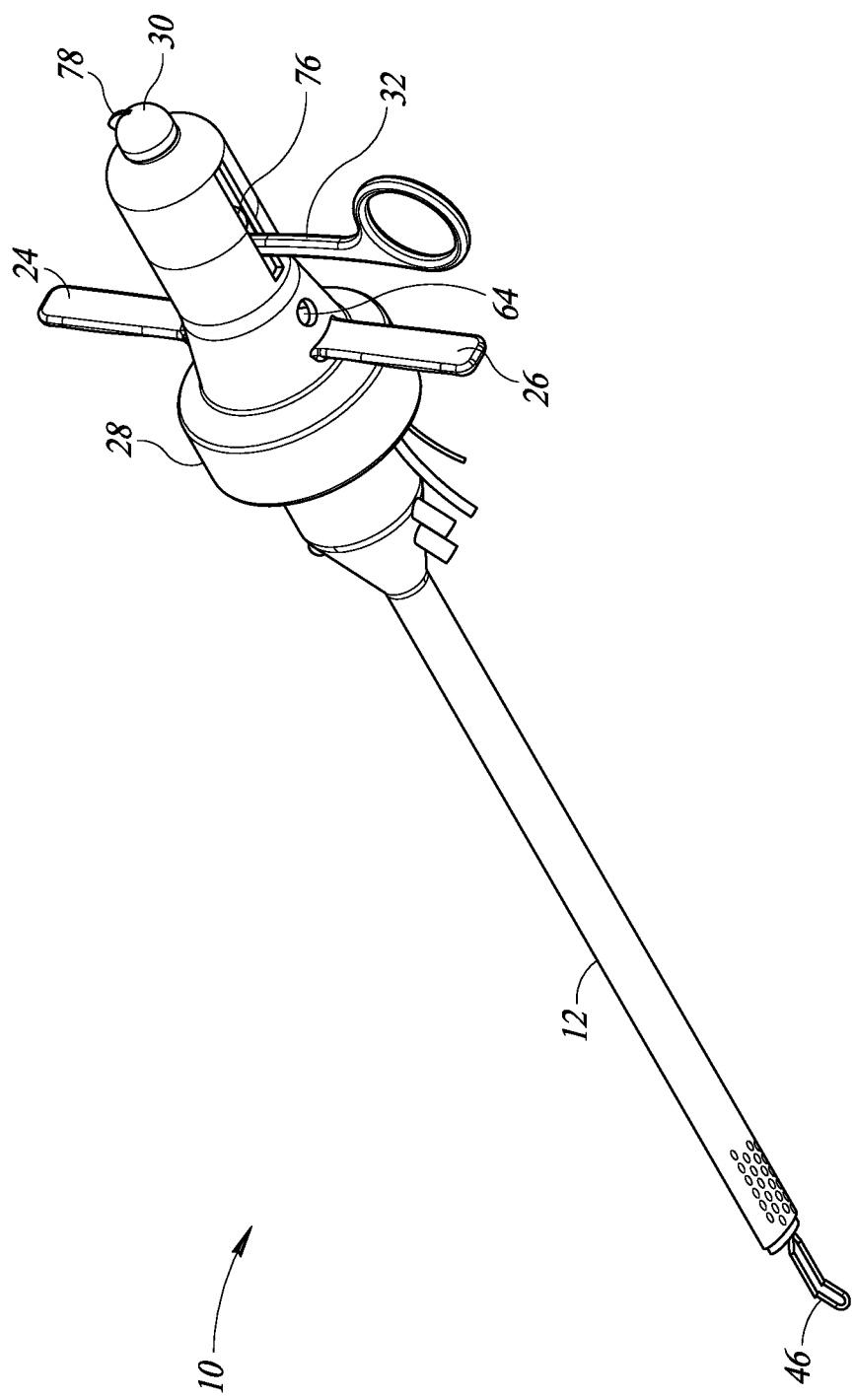
FIG. 7 is a diagram illustrating a perspective view of an example resectoscope of the present invention with the surgical tool extended and rotated to a second position.

A diagram illustrating a perspective view of an example resectoscope of the present invention with the surgical tool extended and rotated to a second position is shown in FIG. 7. With reference to FIG. 7, the loop 46 and trigger 32 of the resectoscope 10 are shown in an extended position and rotated 180 degrees from the position shown in FIG. 6.

Figure 8:
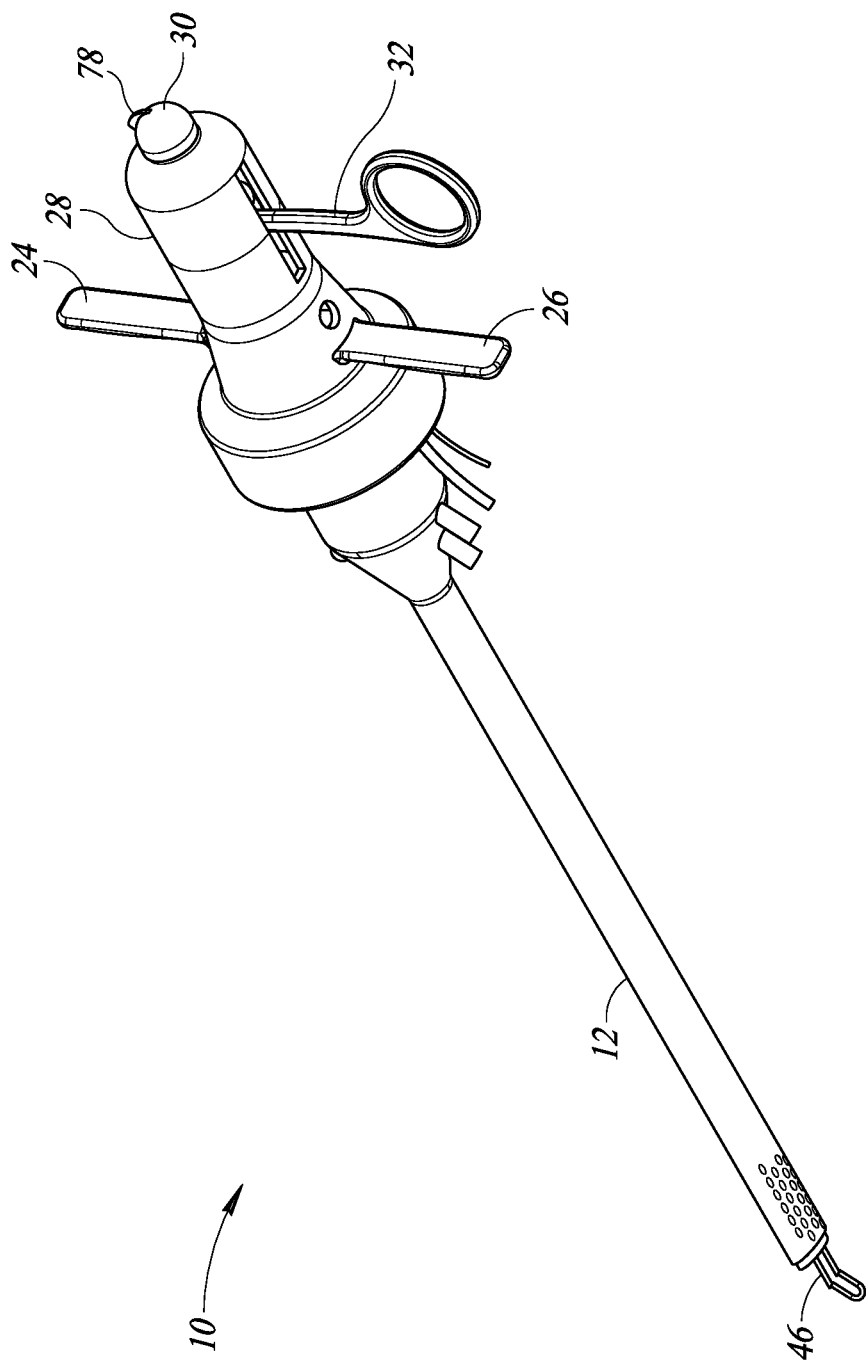
FIG. 8 is a diagram illustrating a perspective view of an example resectoscope of the present invention with the surgical tool retracted.

A diagram illustrating a perspective view of an example resectoscope of the present invention with the surgical tool partially retracted is shown in FIG. 8. With reference to FIG. 8, the loop 46 and trigger 32 are shown retracted and the rotation knob 30 is in the 12 o'clock position.

Figure 9:
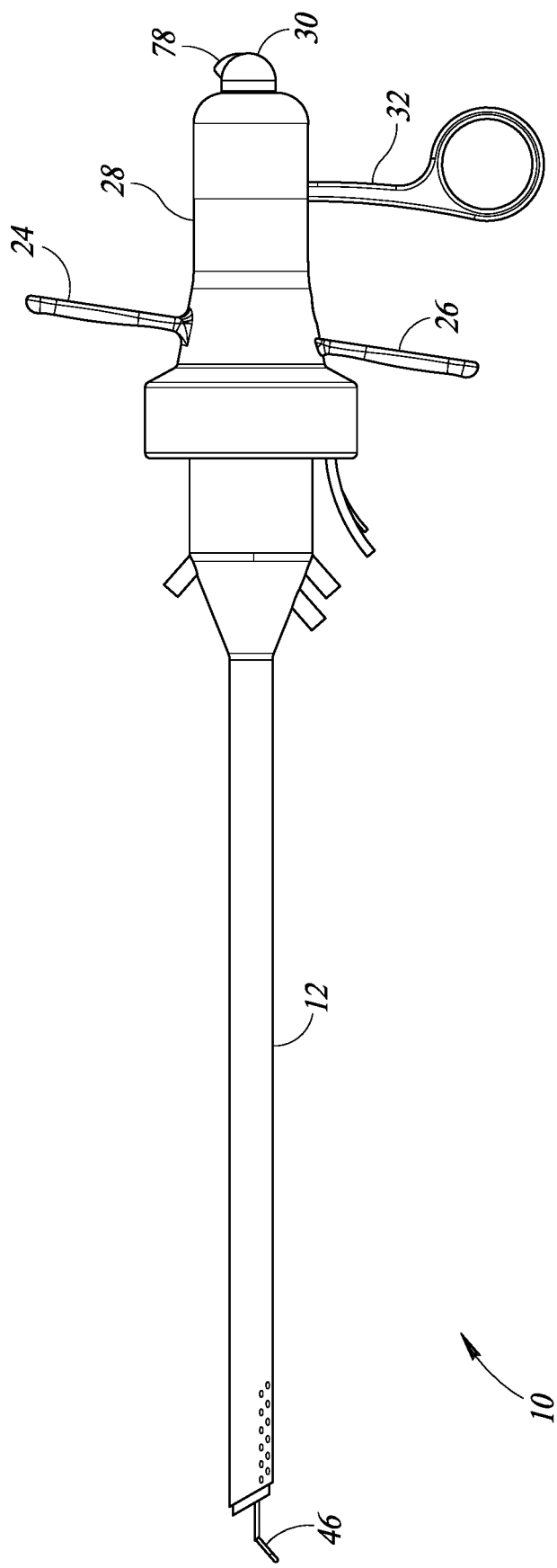
FIG. 9 is a diagram illustrating a side view of an example resectoscope of the present invention with the surgical tool partially retracted.

A diagram illustrating a side view of an example resectoscope of the present invention with the surgical tool partially retracted is shown in FIG. 9. With reference to FIG. 9, the loop 46 and trigger 32 are shown retracted and the rotation knob 30 is in the 12 o'clock position.

Figure 10:
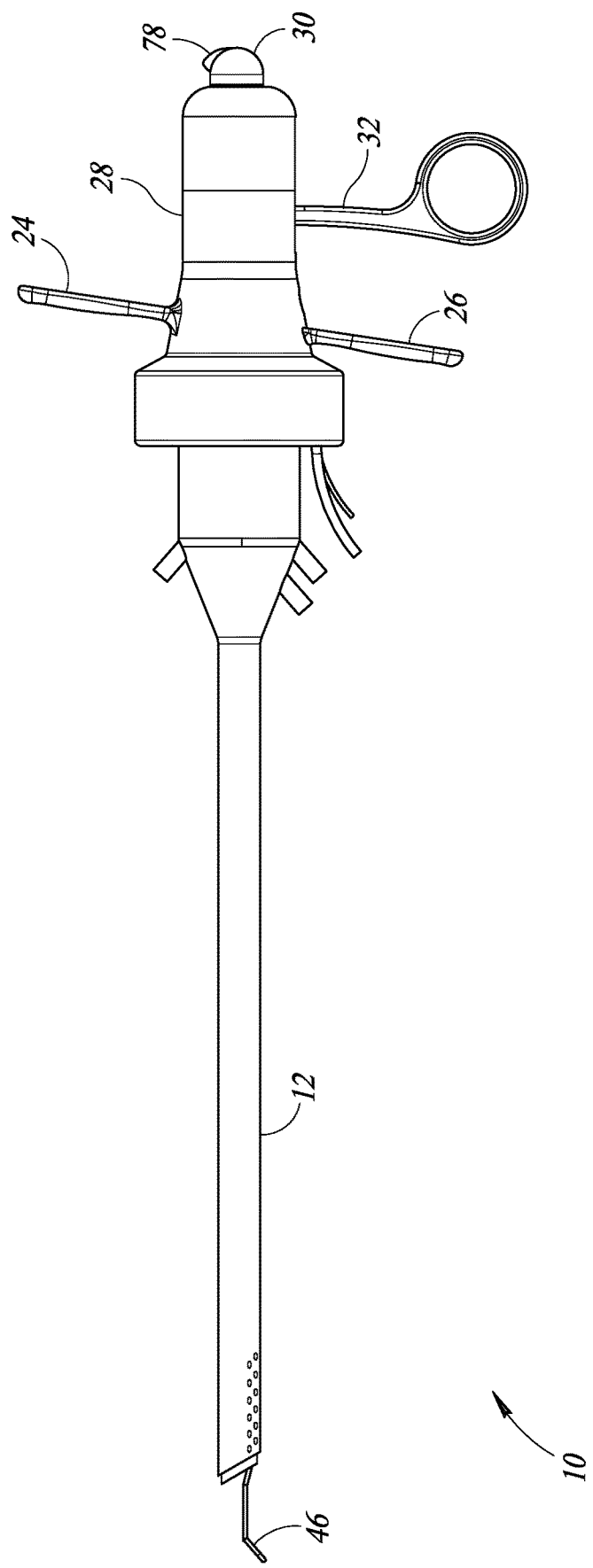
FIG. 10 is a diagram illustrating a side view of an example resectoscope of the present invention with the surgical tool partially extended.

A diagram illustrating a side view of an example resectoscope of the present invention with the surgical tool partially extended is shown in FIG. 10. With reference to FIG. 10, the loop 46 and trigger 32 are shown in an extended position and the rotation knob 30 is in the 12 o'clock position.

Figure 11:
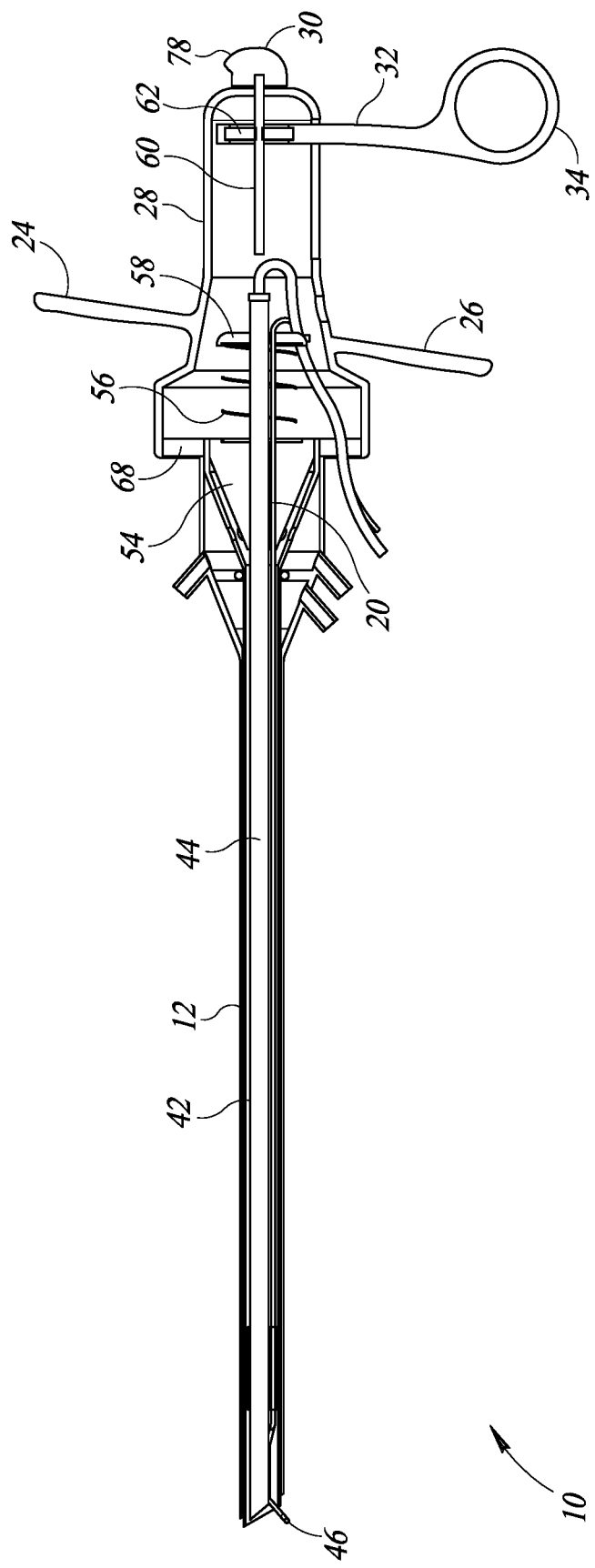
FIG. 11 is a diagram illustrating a cutaway view of an example resectoscope of the present invention with the surgical tool retracted.

A diagram illustrating a cutaway view of an example resectoscope of the present invention with the surgical tool retracted is shown in FIG. 11. With reference to FIG. 11, the loop 46 and trigger 32 are shown in a fully retracted position and the rotation knob 30 is in the 12 o'clock position. In this position, the spring 56 is expanded against collar 58.

Figure 12:
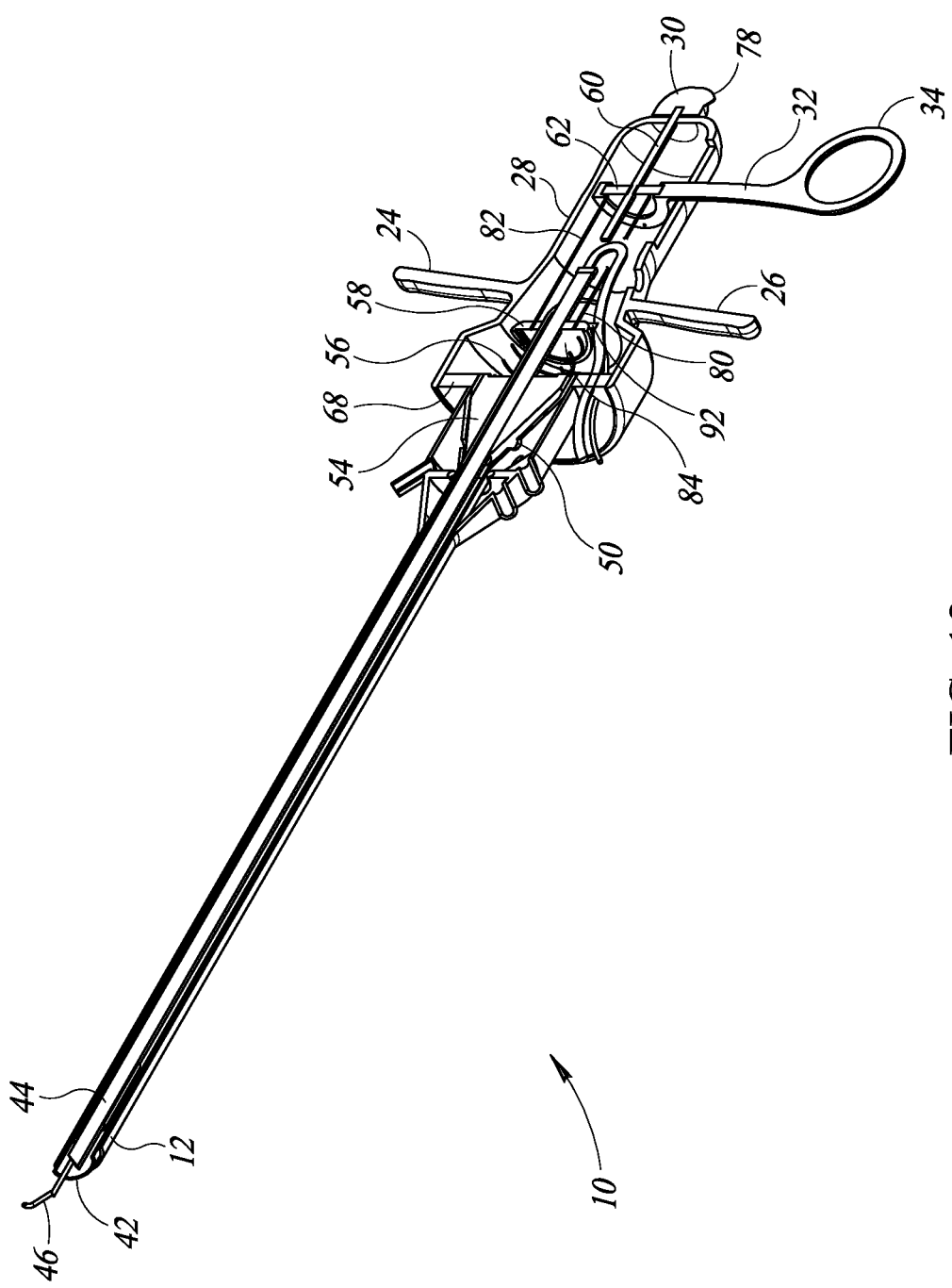
FIG. 12 is a diagram illustrating a perspective cutaway view of an example resectoscope of the present invention with the surgical tool extended.

A diagram illustrating a perspective cutaway view of an example resectoscope of the present invention with the surgical tool extended is shown in FIG. 12. With reference with FIG. 12, the loop 46 and rotation knob 30 are rotated 180 degrees from the position shown in FIG. 5 at the 6 o'clock position.

Figure 13:
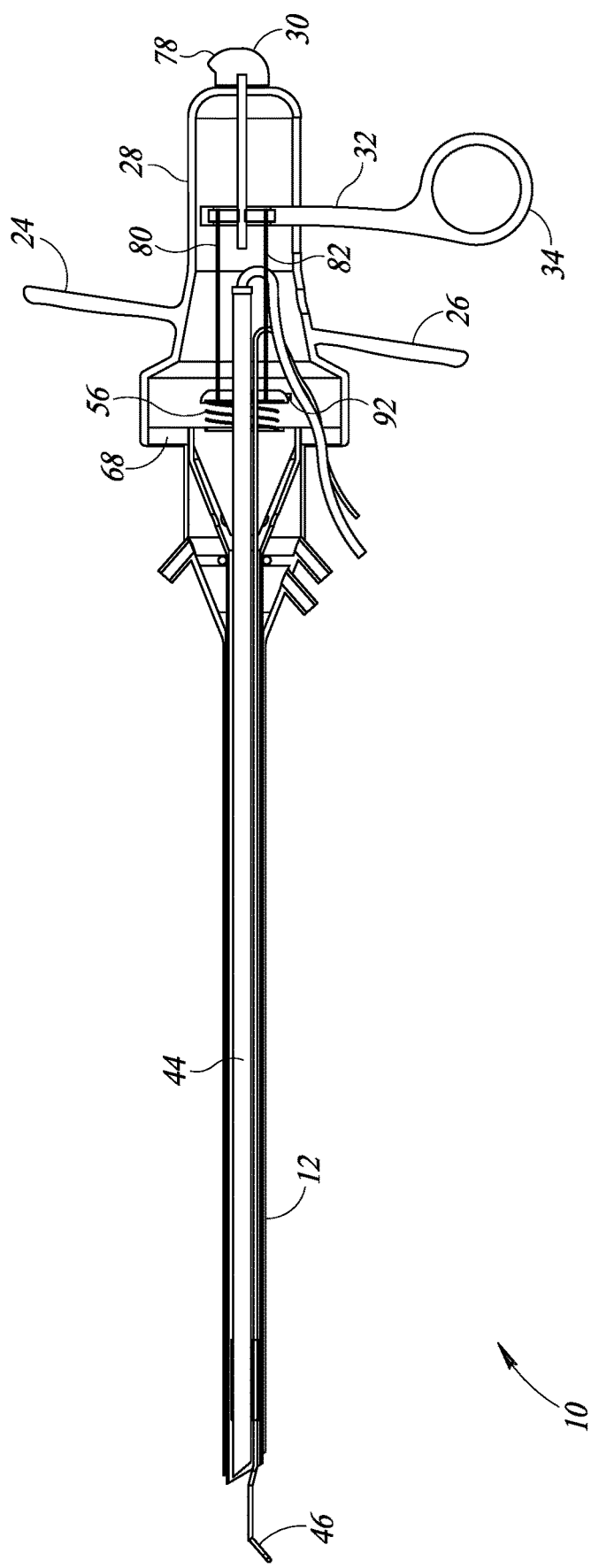
FIG. 13 is a diagram illustrating a side cutaway view of an example resectoscope of the present invention with the surgical tool extended and rotated.

A diagram illustrating a side cutaway view of an example resectoscope of the present invention with the surgical tool extended and rotated is shown in FIG. 13. With reference to FIG. 13, the loop 46 and trigger 32 are shown in an extended position and the rotation knob 30 is in the 12 o'clock position.

Figure 14:
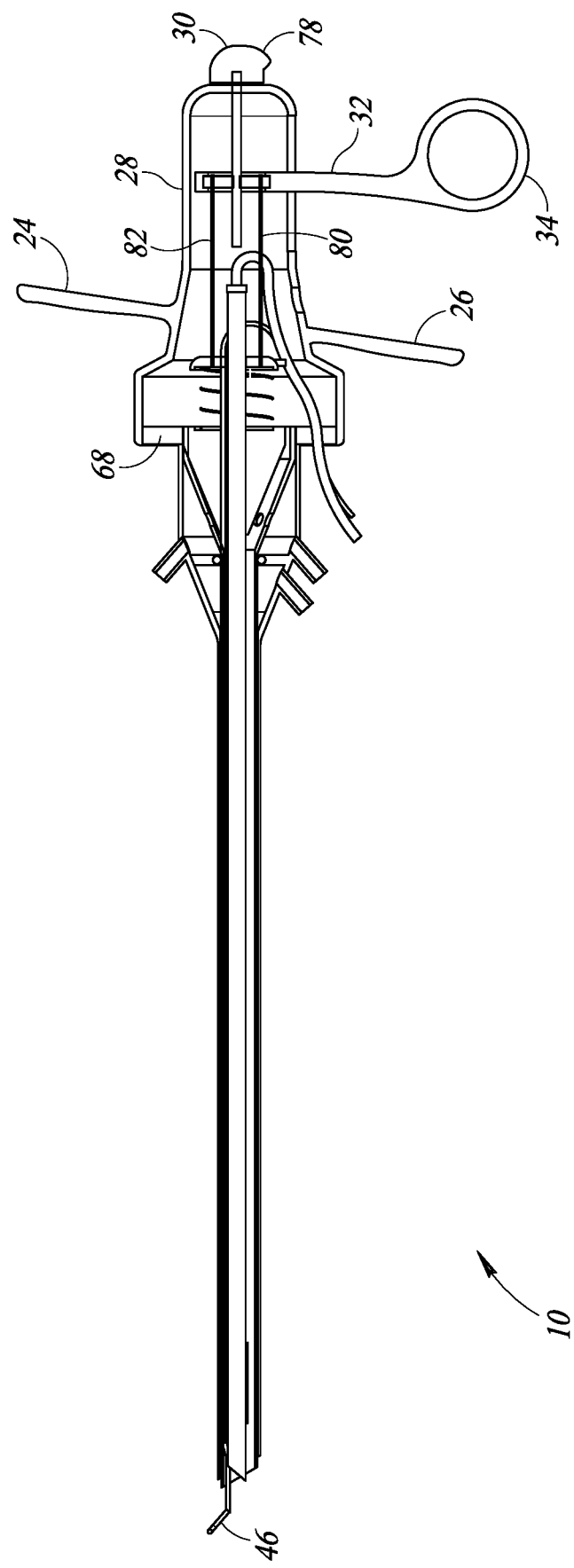
FIG. 14 is a diagram illustrating a side cutaway view of an example resectoscope of the present invention with the surgical tool partially retracted and rotated.

A diagram illustrating a side cutaway view of an example resectoscope of the present invention with the surgical tool partially retracted and rotated is shown in FIG. 14. With reference to FIG. 14, the loop 46 and trigger 32 are shown in a retracted position and the loop 46 and knob 30 are rotated 180 degrees from the position shown in FIG. 5 at the 6 o'clock position.

Figure 15:
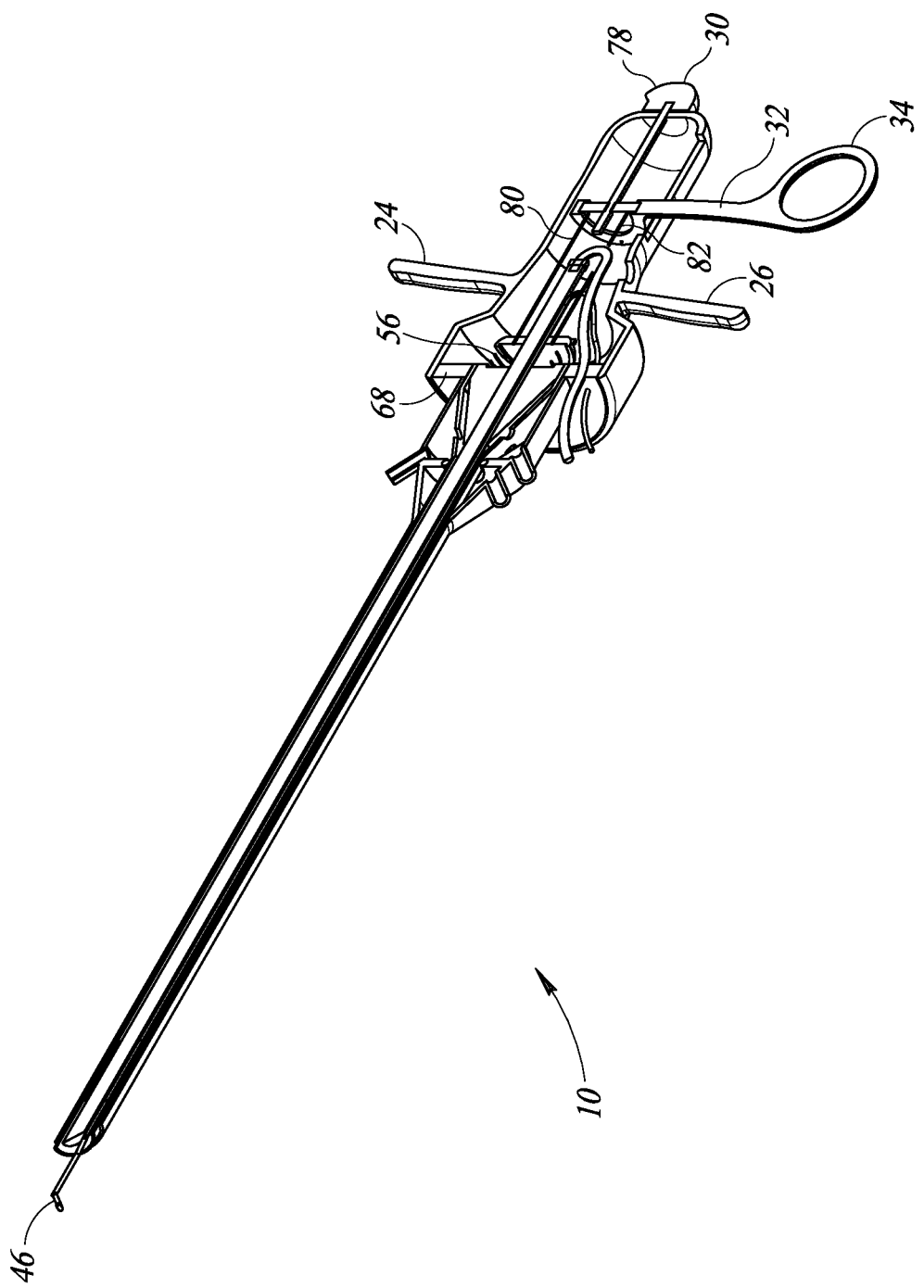
FIG. 15 is a diagram illustrating a perspective cutaway view of an example resectoscope of the present invention with the surgical tool extended.

A diagram illustrating a perspective cutaway view of an example resectoscope of the present invention with the surgical tool extended is shown in FIG. 15. With reference to FIG. 15, the loop 46 and trigger 32 are shown in an extended position and the rotation knob 30 is in the 12 o'clock position.

Figure 16:
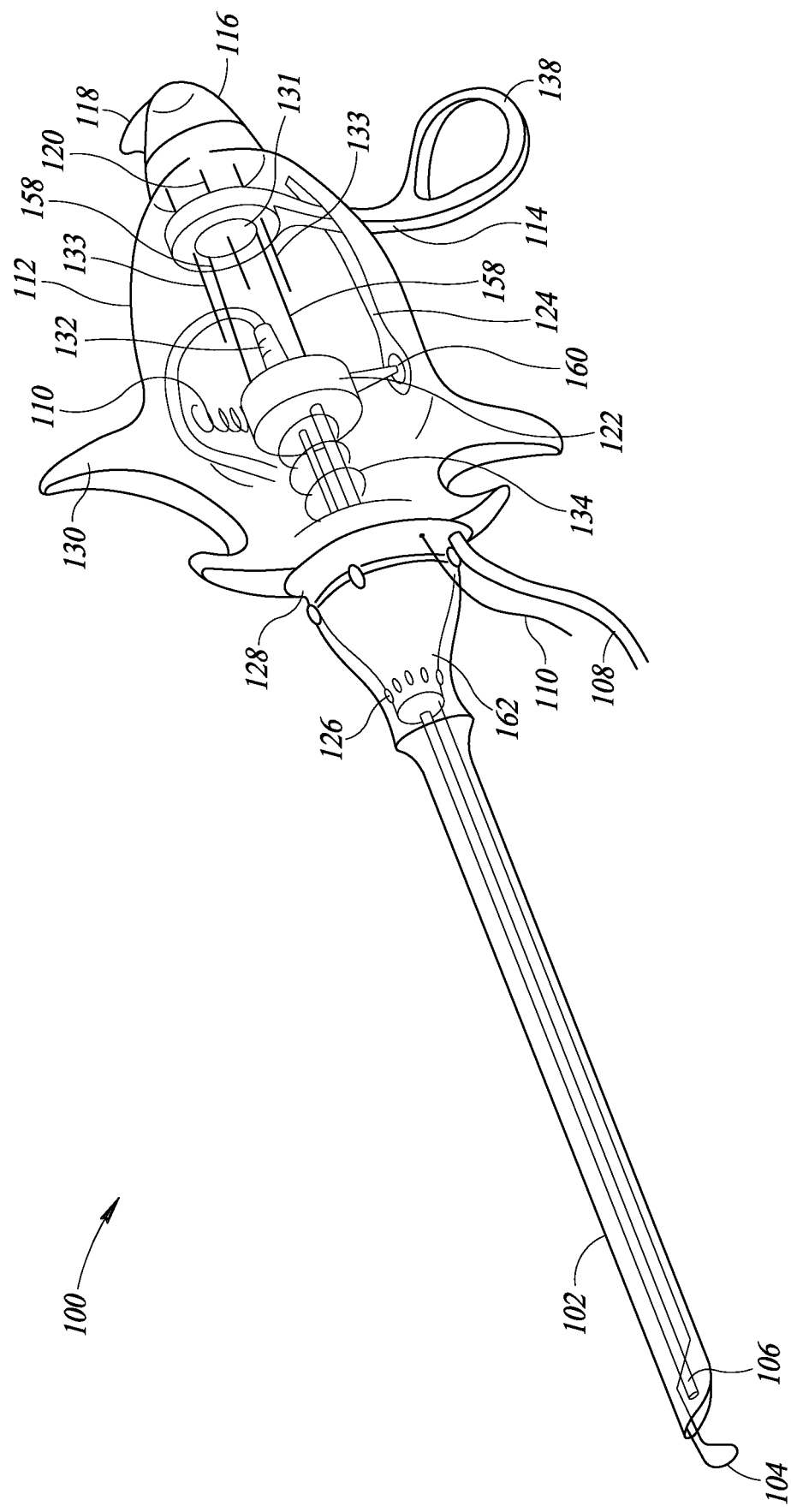
FIG. 16 is a diagram illustrating a perspective view of an example resectoscope of the present invention with the surgical tool partially retracted.

An alternative example embodiment of the resectoscope will now be described. A diagram illustrating a perspective view of an example resectoscope of the present invention with the surgical tool partially retracted is shown in FIG. 16. The resectoscope, generally referenced 100, comprises an inner sheath 102 with holes 126 for irrigation, loop 104, optical tube with lens 106, cone 162, base ring 128 through which optical cable 108 and loop power cable 110 pass through, handle 112, trigger 114 with thumb hole 138, rotation knob 116 with indicator 118, spring 134, collar 122, release pin 160, swivel optical coupler 132, connecting pins 158 for connecting collar 122 with inner disk 131, guide pins 133 affixed to the wall of the handle 112 for guiding the trigger 114 in lateral back and forth motion, and central shaft 120 affixed to the rotary knob for transferring rotational movement of the knob to the inner disk. Note that operation of the resectoscope 100 is similar to that of the resectoscope 10 (FIG. 5) with the addition of two guide pins 133.

Figure 17:
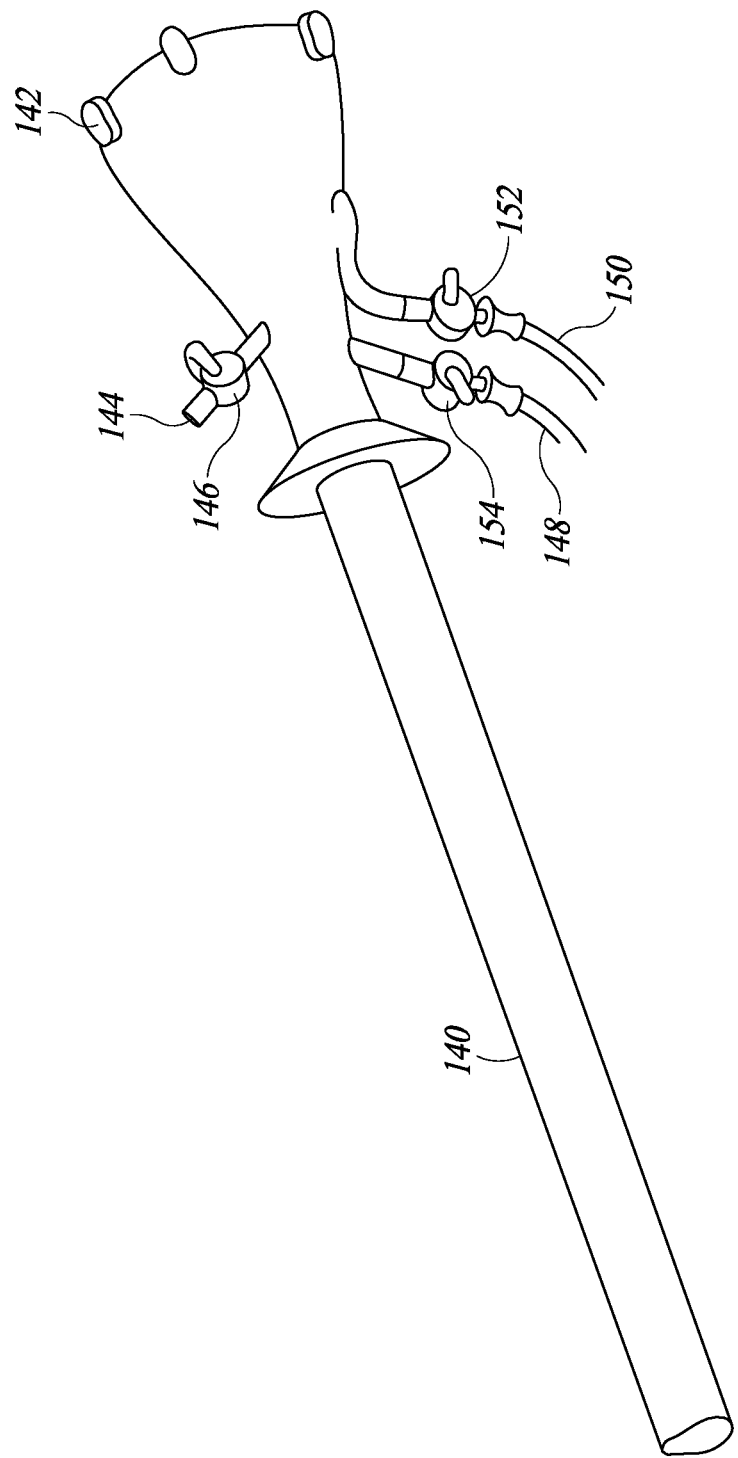
FIG. 17 is a diagram illustrating the outer sheath portion of an example resectoscope of the present invention.

A diagram illustrating the outer sheath portion of an example resectoscope of the present invention is shown in FIG. 17. This Figure illustrates the outer sheath 140 with inlet tubes 144, 150 and corresponding valves 146, 152 as well as outlet tube 148 with corresponding valve 154. Also shown are fasteners 142 for affixing the outer sheath 140 to the base ring 128.

Figure 18:
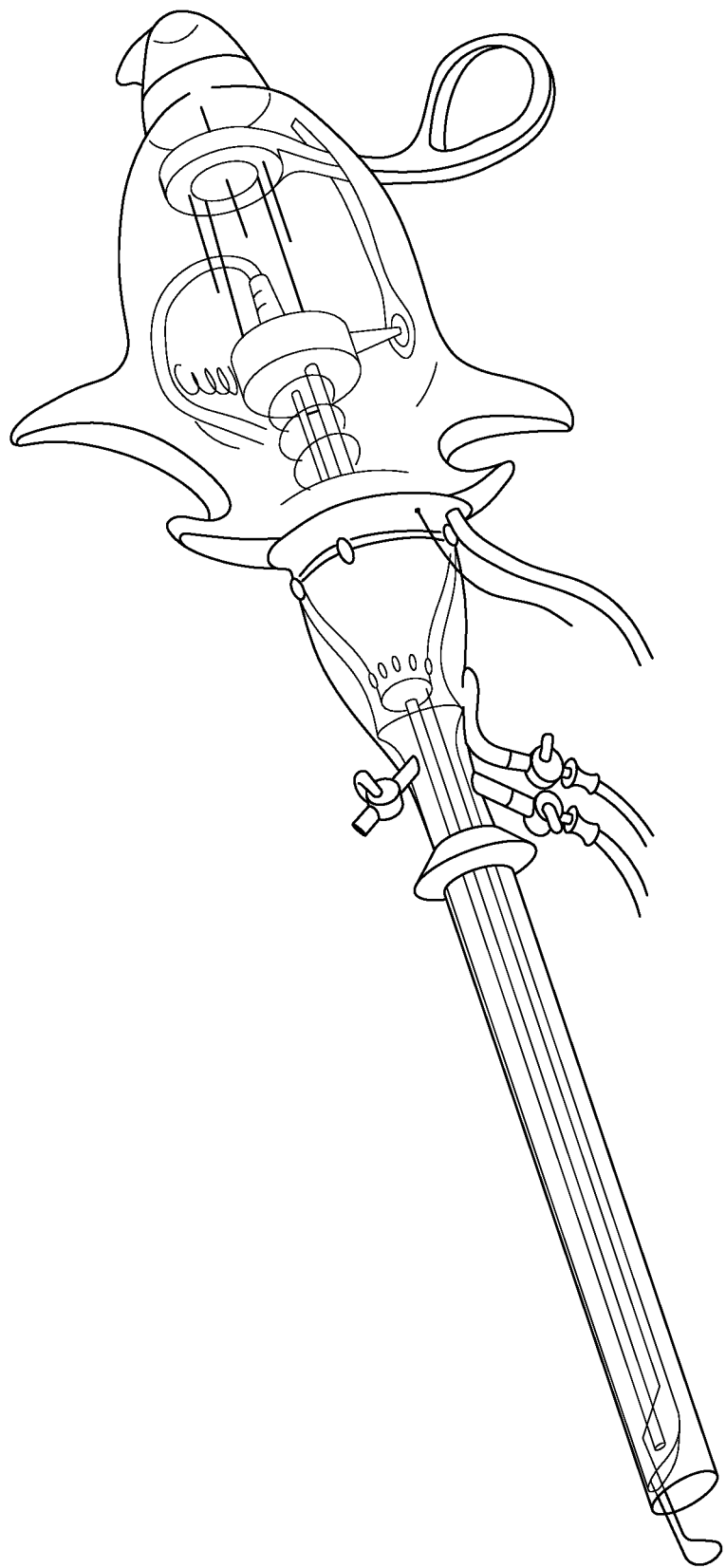
FIG. 18 is a diagram illustrating a perspective view of an example resectoscope of the present invention with the surgical tool partially retracted.

A diagram illustrating a perspective view of an example resectoscope of the present invention with the surgical tool partially retracted is shown in FIG. 18. This Figure shows the resectoscope completely assembled with the outer sheath attached to the base ring. Similar to the resectoscope 10 (FIG. 5), the resectoscope 100 transfers rotation of the knob to rotation of the optical tube, loop and inner sheath, which rotate as a single entity. Rotation of the knob and optical tube, loop and inner sheath is independent of rotation of the handle. Thus, rotation of the handle is independent of rotation of the knob, optical tube, loop and inner sheath. Lateral back and forth movement of the trigger causes the loop to move laterally in unison with the trigger motion thereby extending and retracting it from the inner sheath.

Figure 19:
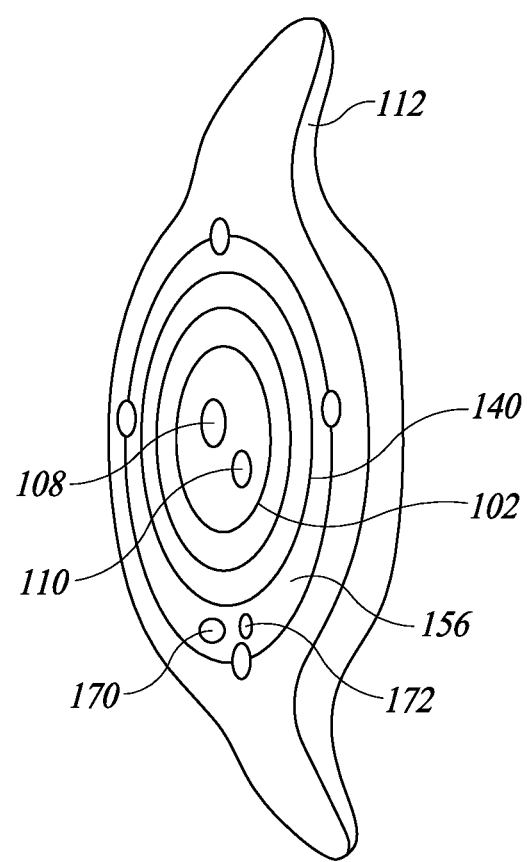
FIG. 19 is a diagram illustrating a perspective view of an example base ring of the present invention.

A diagram illustrating a perspective view of an example base ring of the present invention is shown in FIG. 19. This Figure illustrates a perspective view of a section taken through the base ring near the left end of the handle. Hole 110 is for the loop power cable while hole 108 is for the optical tube. Both the loop cable and optical tube are located within the inner sheath 102. The inner sheath is located within the outer sheath 140. The base ring 156 has two perforations 170, 172 for the optical cable and loop power cable, respectively. The left end portion of the handle 112 is the outermost element shown.

Figure 20:
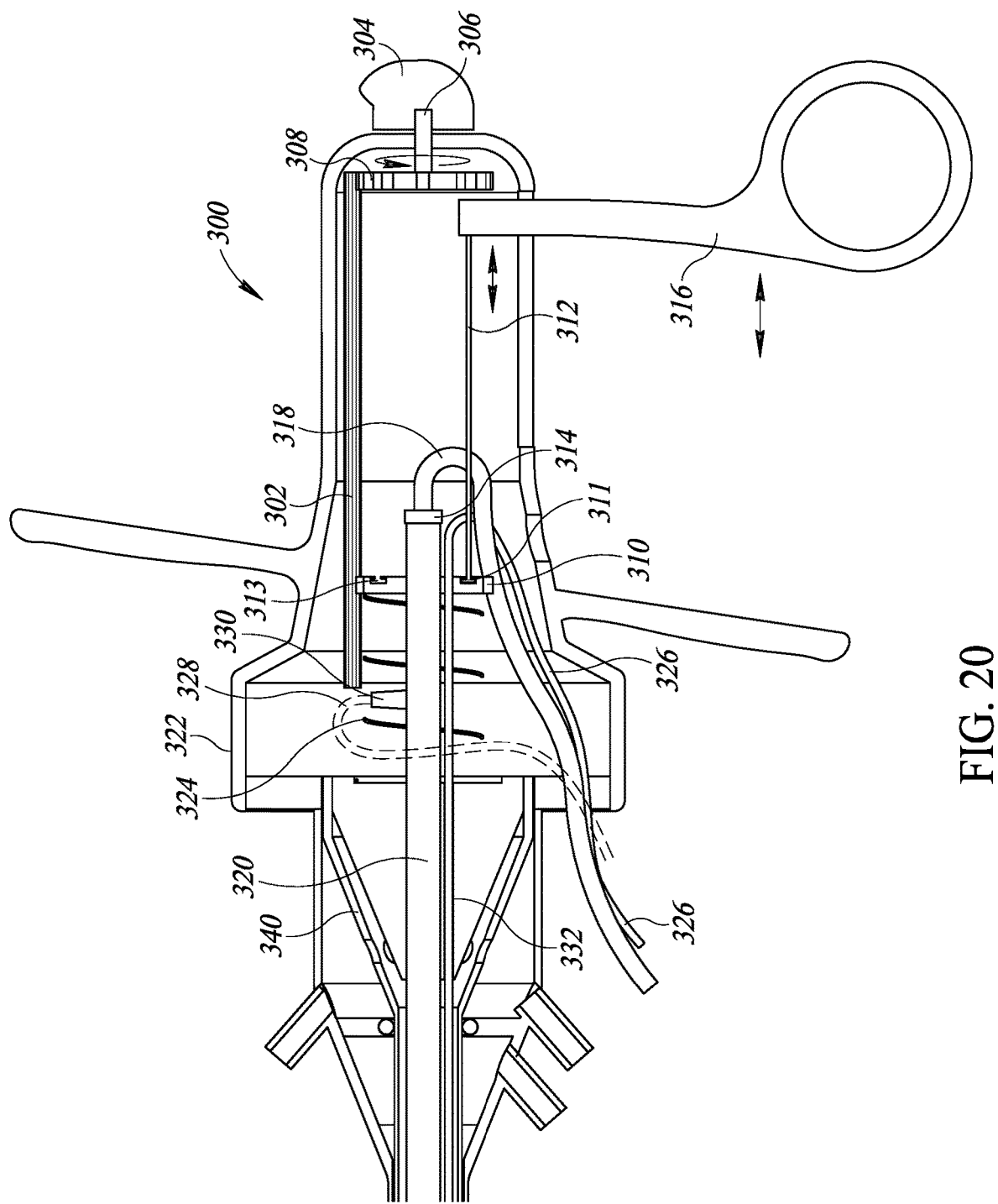
FIG. 20 is a diagram illustrating a side cutaway view of an example resectoscope of the present invention with its trigger in the retracted position.

A diagram illustrating a side cutaway view of an example resectoscope of the present invention with its trigger in the retracted position is shown in FIG. 20. In this alternative embodiment, the resectoscope, generally referenced 300, comprises the inner and outer sheath as in resectoscope embodiments described supra. A difference is the mechanism used to transfer rotation from the knob to the collar. In this embodiment, rotation of the knob 304 is transferred to rotation of the collar 310 via a gear mechanism. Toothed shaft 302 is an elongated gear with teeth that mesh with teeth on gear 308 and teeth on the collar 310. Turning knob 304 causes gear 308 to turn via shaft 306. This turns elongated toothed shaft 302 to turn which in turn causes the toothed collar 310 to turn, thus rotating the optical tube 320, loop cable 332, and inner sheath 340. Optical tube 320 is free to rotate without binding the optical cable 318 due to the swivelable rotary optical coupler 314.

In addition, electrical power to the loop can be conveyed using a well-known slip ring type connection 330 such as used in electrical motors, etc. Examples of slip ring connections include, mercury rotating connector, pancake slip ring, rotary band contact, rotary power transfer device, rotary transformer, rotating continuity device, and rotating electrical connector. Use of a slip ring connection eliminates the need for the power cable 326 to extend deep into the handle 322. Rather, the cable 326 can be routed to the slip ring connection via the dashed line cable 328.

In addition, in one embodiment, the optical tube, if constructed from metal can be used to transfer electrical power to the electrode loop. Using such an arrangement makes the optical tube the open element that is required to pass through the collar. Element 332 mechanically connected to the loop would still be required to extend and retract the loop via lateral motion of the trigger 316.

In operation, lateral motion of the trigger 316 causes the collar to move laterally due to the connecting pin or rod 312 connecting the collar to the trigger. In one embodiment, the rod 312 is not permanently affixed to the collar but rather rests on the side surface of the collar. The force of the spring 324 keeps the trigger and the loop in the retracted position. Lateral force on the trigger 316 by the user causes rod 312 to push against the collar thereby compressing spring 324 and extending the loop. Not permanently affixing the rod 312 to the collar 310 allows the collar to rotate freely while still reacting to lateral forces on the trigger. Once extended, the loop, element 332, rod 312, collar 310, and trigger 316 are all moved back to the retracted position by the decompression of the spring 324 once the user removes or reverses the lateral force on the trigger.

In an alternative embodiment, the rod 312 is coupled to the collar via a T connection whereby the end of the rod has a T shape that fits a complementary T shaped recessed ring 313 in the surface of the collar, as shown in FIG. 20. The recessed ring holds the T shaped end of the rod while allowing the collar to rotate freely. Lateral motion of the trigger, however, is transferred to the collar thereby compressing spring 324 and extending the loop.

Using this gear mechanism thus permits the combination of the optical tube, element 332 and inner sheath to rotate independently of the position of the handle 322 while at the same time allowing for the extension and retraction of the loop independent of the position of the handle and of the rotation orientation of the combination of the optical tube, element 332 and inner sheath.

Figure 21:
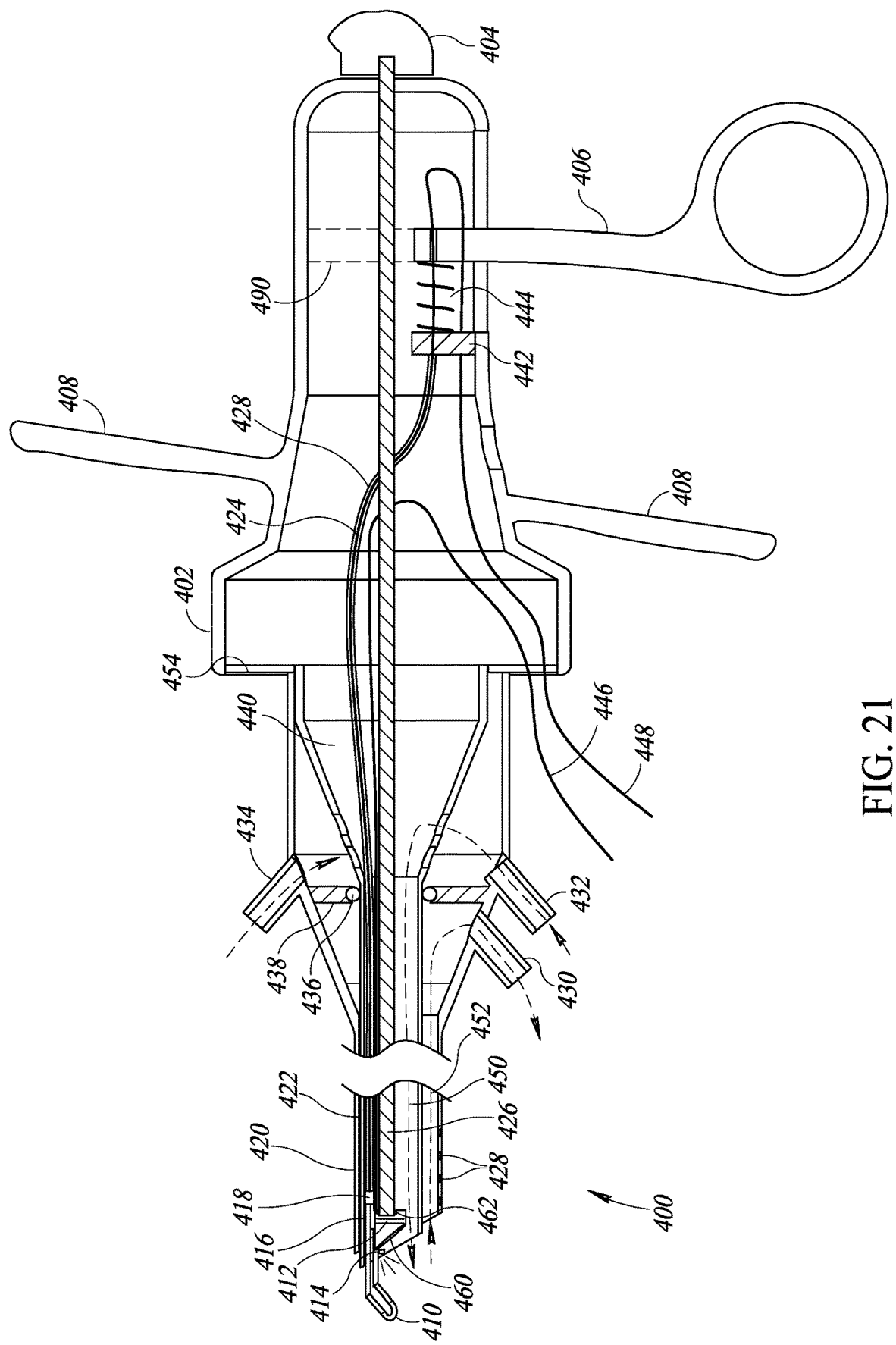
FIG. 21 is a diagram illustrating a side cutaway view of an example resectoscope of the present invention with the surgical tool extended.

A diagram illustrating a side cutaway view of an example resectoscope of the present invention with the surgical tool extended is shown in FIG. 21. In this alternative embodiment, the resectoscope, generally referenced 400, comprises the inner sheath 422 and outer 420 sheath as in resectoscope embodiments described supra. At the end of the inner sheath resides a rotary encoder 462, video camera 412, lens 460 and LED lighting 414. Rotation of the loop 410 and camera is achieved by turning the knob 404 and shaft 426. Lateral back and forth of the loop 410 is achieved using a cable 428 inside a sheath 424. Stops 442 and 418 terminate the sheath 424 while letting the cable pass through. Spring 444 functions to provide tension. The cable 428/448 also functions to provide electrical power to the loop. Electrical cable 446 carries electrical power for the LED, output video signals and output rotary encoder signals. Rotation of the combination of inner sheath 422 and its contents is similar to the previous embodiments. Note, however, that although full 360-degree rotation is achieved, there is a stop 462 preventing multiple 360-degree rotations of the knob.

The trigger 406 is actuated by the user which causes compression of the spring 444 and outward movement of the loop 410. Optionally, the trigger element 406 can be extended to the top of the handle (i.e. dashed portion 490) where the end of the extended trigger is fastened to the inside of the handle so as to allow the trigger to pivot forwards and backwards. An elongated vertical opening in the extended portion of the trigger allows it to pivot back and forth without binding or otherwise interfering with the rotation of the shaft 426.

As in embodiments described supra, fluid inlets 432, 434 and outlet 430 provide irrigation liquid that flows through the inner and outer sheathes as shown by dashed lines 450, 452, respectively.

Figure 22B:
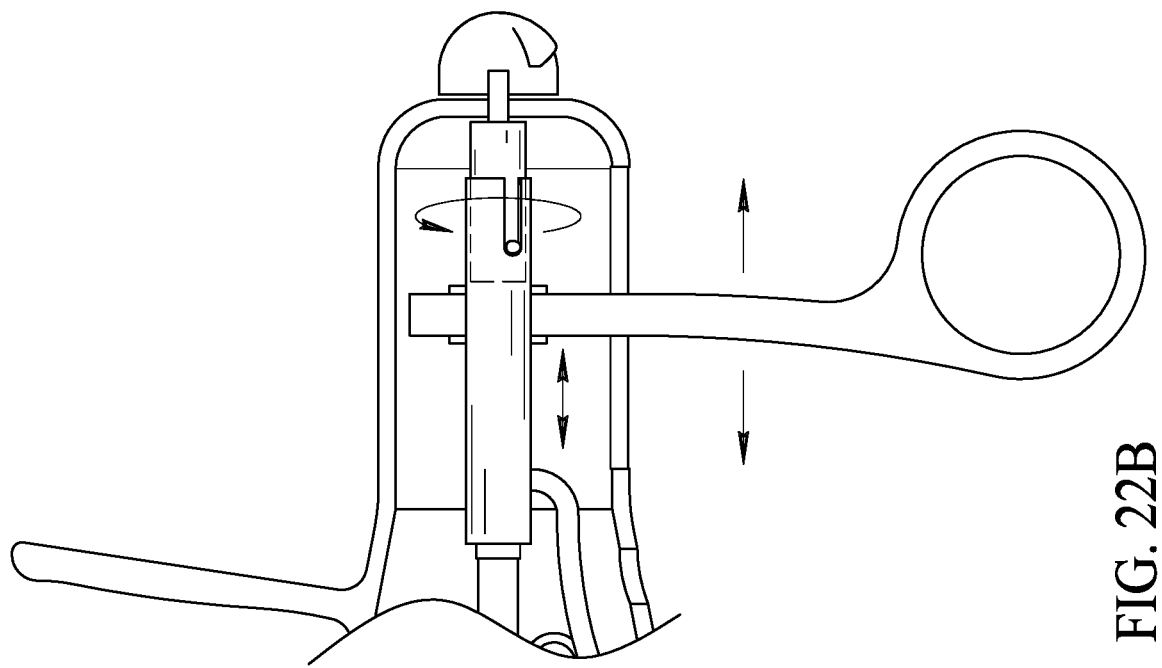
FIG. 22B is a diagram illustrating a side cutaway view of an example resectoscope of the present invention with the surgical tool partially extended and rotated.
Figure 22A:
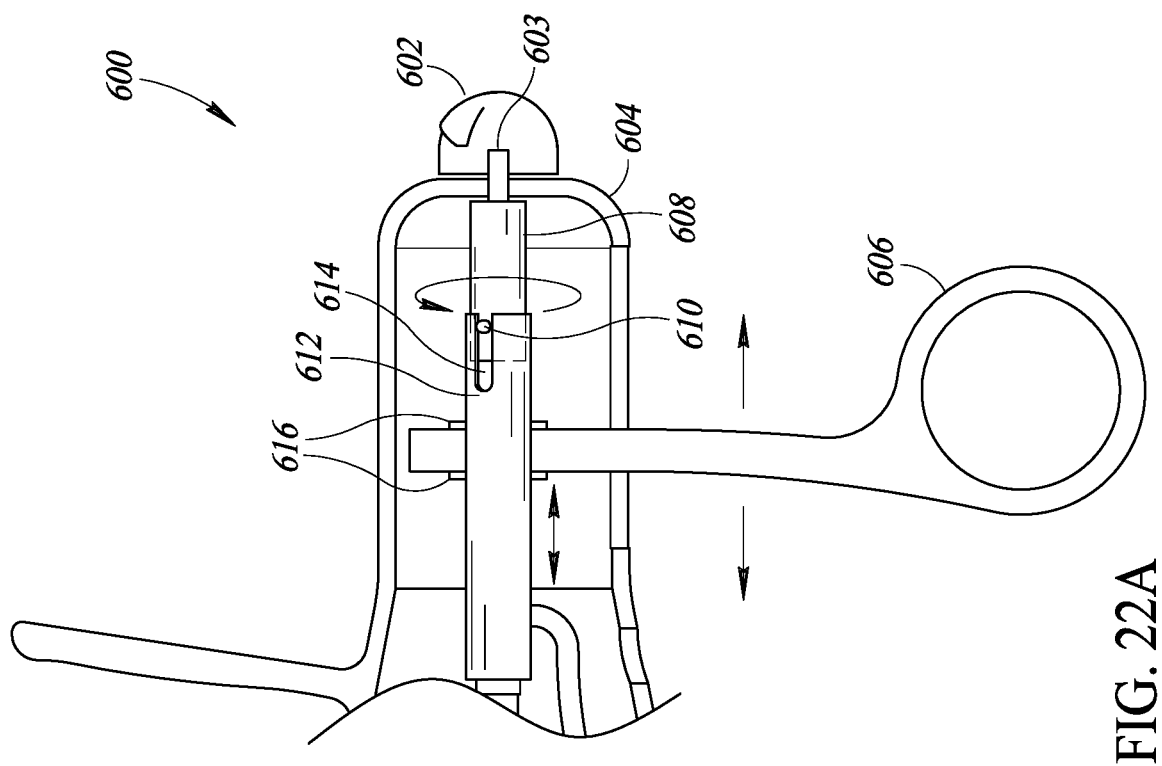
FIG. 22A is a diagram illustrating a side cutaway view of an example resectoscope of the present invention with the surgical tool partially extended.

A diagram illustrating a side cutaway view of an example resectoscope of the present invention with the surgical tool partially extended is shown in FIG. 22A. In this alternative embodiment, a rotation mechanism based on a slip joint is used. The rotation mechanism comprises the connecting tube 612, drive shaft 608, connecting pin 603, rotation knob 602 and drive pin 610. All these components are coupled to or located within handle assembly 604.

In operation, when a user turns the rotation knob 602, the rotation energy is transferred through the connecting pin 603 to drive shaft 608. Drive pin 610 extends through the drive shaft 608 and a bit beyond sufficient to hold the drive shaft stationary with respect to the connecting tube 612. The connecting tube comprises a pair of slits 614 approximately 180 degrees apart adapted to receipt the drive pin 610. The slip joint is operative to transfer rotational force from the drive shaft to the connecting tube. The connecting tube is adapted to transfer rotational energy to the inner sheath including optical tube and loop (not shown).

Lateral movement of the trigger 606 causes the connecting tube 612 to move laterally along the axis of the optical tube. Regardless of the position of the trigger (i.e. extended or retracted), the drive shaft and connecting tube are free to rotate independent of the position of the trigger. Movement of the trigger causes the drive pin 610 to move in and out of the slits 614. The connecting tube is free to rotate regardless of the position of the trigger due to the washers (i.e. stops) 616 and affixed to the connecting tube on either side of the trigger element. The trigger element comprises a forked portion (see FIG. 22C) wherein the connecting tube sits within the inside of the fork. The washers 616 act as stops for the trigger transferring lateral motion of the trigger to lateral motion of the connecting tube.

A diagram illustrating a side cutaway view of an example resectoscope of the present invention with the surgical tool partially extended and rotated is shown in FIG. 22B. In this Figure, the trigger 606 is shown in a partially retracted position and the rotation knob in a different position than that shown in FIG. 22A. As described supra, the slip joint enables lateral motion of the inner sheath including optical tube and loop independent from the rotation thereof.

Figure 22C:
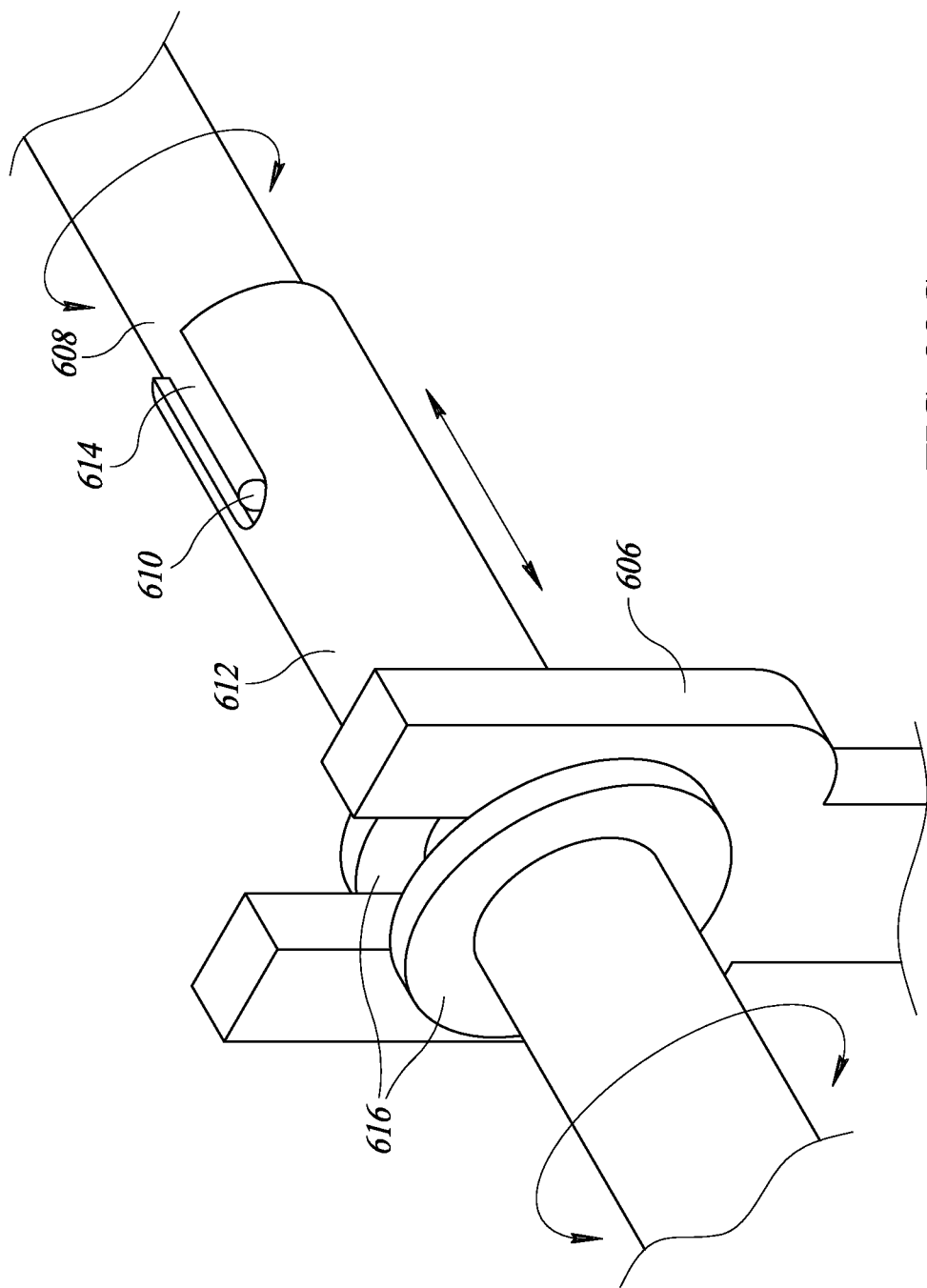
FIG. 22C is a diagram illustrating a perspective view of the slip joint and trigger portion of the resectoscope in more detail.

A diagram illustrating a perspective view of the slip joint and trigger portion of the resectoscope in more detail is shown in FIG. 22C. The forked portion of the trigger 606 is adapted to straddle the width of the connecting tube 612 in between the two washers 616. The drive shaft 608 and connecting tube 612 are free to rotate indecently of the lateral movement of the trigger 606. Movement of the trigger back and forth is transferred to lateral motion of the connecting tube 612.

While certain embodiments have been described herein, other embodiments are also possible. For example, the principles of the invention are not restricted to resectoscopes, but are equally applicable to endoscopic and laparoscopic tools requiring rotational movement. In particular, the principles of the invention can be applied to cystoscopes (bladder), bronchoscopes (lungs), and colonoscopes (colon).

The technology described herein is directly applicable to and may be advantageous to all manner of laparoscopic or minimally invasive surgery, extending to the general surgical, gynecologic, obstetric, neurosurgical, endoscopic including gastrointestinal, airway intubation with video or without video assistance, and ear, nose, and throat (ENT) fields. A rotational and lateral movement mechanism as described supra stands to be beneficial for similar ergonomic and safety related reasons in all of the fields mentioned as well as any new or emerging field of procedure that employs an instrument meant to extend and/or resect, treat, and/or manipulate or apply a treatment within the full spectrum of instrument rotation, including up to 360-degrees of rotation or beyond, particularly when the use of a light source is concurrently required.

While the use of a rotation and lateral motion mechanism has been described, other types of rotation and lateral motion mechanisms can be used to rotate and move the loop laterally independent of the handle. For example, a gear and shaft mechanism can be used to transfer rotation of the knob to the collar.

Regarding the disposability of the resectoscope of the present invention, each of the embodiments presented supra is applicable to be manufactured from plastics, e.g., polymers. Preferably, medical grade plastic materials that meet FDA and USP Class VI requirements should be used. Polymers are well suited to disposable medical devices as they offer lighter weight, better biocompatibility and lower cost. Fibers and resins used to manufacture medical instruments include polyvinyl chloride (PVC), polypropylene (PP), polyethylene (PE), high density polyethylene (HDPE), low density polyethylene (LDPE), polystyrene (PS) as well as nylon, polyethylene terephthalate (PET), polyethylene terephthalate glycol-modified (PETG), polyimide (PA), polybutylene terephthalate (PBT), polycarbonate (PC), acrylonitrile butadiene (ABS), polyetheretherketone (PEEK), acetal, polyurethane (PU), Rulon®, Polymide, Surlyn®, Proflex®, TPX®, PPS, Torlon®, Polysulfone, Celazole®, Orkot®, Ultem®, Fluorosint®, Semitron®, Noryl®, and Kynar® PVDF. Most commonly, the plastic material used in medical applications is PVC followed by PE, PP, PS and PET. PVC is mostly used in pre-sterilized single use medical applications.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediary components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the claims, any reference signs placed between parentheses shall not be construed as limiting the claim. The use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first," "second," etc. are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A surgical device, comprising:
    a conduit having a longitudinal axis and being configured to extend into a body cavity;
    a handle incorporating a trigger, said handle and said trigger rotatably coupled to said conduit and operative to rotate freely independently from said conduit;
    a surgical tool slidably received in and aligned parallel to the longitudinal axis of said conduit, said surgical tool operative to rotate freely within said conduit and selectively extend laterally from said conduit under control of said trigger; and
    a rotation mechanism coupled to said surgical tool, said rotation mechanism operative to enable a user to rotate said surgical tool independently from a position of said handle and trigger as well as lateral extension of said surgical tool.

2. The surgical device according to claim 1, wherein said trigger coupled to said surgical tool whereby lateral motion of said trigger causes lateral motion of said surgical tool.

3. The surgical device according to claim 1, wherein said surgical tool comprises an electrode loop.

4. The surgical device according to claim 1, wherein said rotation mechanism comprises a rotation knob coupled thereto and accessible by a user, whereby rotation of said rotation knob causes rotation of said surgical tool independent of said handle.

5. The surgical device according to claim 1, wherein said rotation mechanism comprises a collar affixed to said surgical tool.

6. The surgical device according to claim 1, wherein one or more irrigation hoses, optical cables, and electrical cables coupled to said surgical device via said conduit remain stationary relative to rotation of said surgical tool.

7. The surgical device according to claim 1, further comprising a light source configured to illuminate said surgical tool and the area surrounding it.

8. The surgical device according to claim 1, further comprising an imaging device rotatable with said surgical tool and configured to enable the user to view a working area of said surgical tool.

9. The surgical device according to claim 1, further comprising a cord containment system operative to allow all cordage to remain stationary thereby substantially reducing cord entanglement.

10. The surgical device according to claim 1, wherein said conduit, said handle, and said rotation mechanism are adapted to be produced from disposable plastic material.

11. The surgical device according to claim 1, wherein said rotation mechanism is operative to allow a surgeon's hand to remain in an ergonomically neutral position while treating lesions in a patient's body.

12. The surgical device according to claim 1, wherein said rotation mechanism comprises a base ring including an outer portion fitted to said handle and an inner portion fitted to said an inner sheath containing said surgical tool, whereby said handle is able to freely rotate independently of said inner sheath.

13. The surgical device according to claim 1, wherein said rotation mechanism comprises a gear mechanism operative to transfer rotation from a knob used to control rotation of said surgical tool to a collar coupled to an inner sheath containing said surgical tool.

14. The surgical device according to claim 1, wherein said rotation mechanism comprises a shaft coupling a control knob to said surgical tool and a camera.

15. The surgical device according to claim 1, wherein said rotation mechanism comprises a slip joint operative to transfer rotational force from a drive shaft to connecting tube which in turn transfers rotational energy to an inner sheath containing said surgical tool.

16. A surgical device, comprising:
    a conduit having a longitudinal axis and being configured to extend into a body cavity;
    a handle rotatably coupled to said conduit and incorporating a trigger;
    a surgical tool aligned parallel to the longitudinal axis of said conduit and capable of both rotating within said conduit and selectively extending laterally from said conduit;
    said trigger coupled to said surgical tool and operative to provide a user controlled linear movement of said surgical tool while allowing simultaneous independent rotation thereof; and
    a rotation mechanism coupled to said surgical tool and said trigger, said rotation mechanism operative to enable a user to control the rotation of said surgical tool independent of a position of said handle and said trigger and independent of lateral extension of said surgical tool as controlled via said trigger.

17. A surgical device comprising:
a base ring having an inner portion, outer portion and side portion;
an outer sheath having a longitudinal axis and configured to extend into a body cavity, said outer sheath affixed to said side portion of said base ring and having inlet and outlet irrigation ports;
an inner sheath having a longitudinal axis and placed within said outer sheath, said inner sheath rotatably coupled to said inner portion of said base ring;
a surgical tool located within said inner sheath;
a handle rotatably coupled to said outer portion of said base ring;
a collar affixed to said surgical tool;
a rotation knob coupled to said collar whereby rotation of said knob causes rotation of said inner sheath and surgical tool independent of rotation of said handle; and
a trigger coupled to said collar whereby lateral motion of said trigger causes lateral motion of said surgical tool while said inner sheath remains stationary.

18. The surgical device according to claim 17, further comprising an optical tube located within said inner sheath, wherein rotation of said rotation knob causes rotation of said optical tube along with said surgical tool.

19. The surgical device according to claim 17, wherein said surgical tool comprises an electrode loop.

20. The surgical device according to claim 17, wherein one or more hoses and cables coupled to said surgical device via said outer sheath remain stationary relative to rotation of said surgical tool.

21. The surgical device according to claim 17, further comprising a light source configured to illuminate said surgical tool and the area surrounding it.

22. The surgical device according to claim 17, further comprising an imaging device rotatable with said surgical tool and configured to enable the user to view a working area of said surgical tool.

23. A method for examination or treatment within a body cavity of a patient utilizing a surgical device, wherein the surgical device comprises:
a conduit having a longitudinal axis and being configured to extend into the body cavity;
a handle incorporating a trigger, said handle and said trigger rotatably coupled to said conduit and operative to rotate freely independently from said conduit;
a surgical tool slidably received in and aligned parallel to the longitudinal axis of said conduit, said surgical tool operative to rotate freely within said conduit and selectively extend laterally from said conduit under control of said trigger;
a rotation mechanism coupled to said surgical tool, said rotation mechanism operative to enable a user to rotate said surgical tool independently from a position of said handle and trigger as well as lateral extension of said surgical tool;
the method comprising:
inserting said surgical device into the body cavity of the patient such that the surgical device extends therein;
gripping said handle in a desired position without regard to the position of said surgical tool; and
rotating said surgical tool to a desired position independent of a position of said handle.

24. The method according to claim 23, wherein one or more hoses and cables coupled to said surgical device via said conduit remain stationary relative to rotation of said surgical tool.

25. The method according to claim 23, wherein said surgical device further comprises a light source configured to illuminate said surgical tool and the area surrounding it.

* * * * *